United States Patent [19]

Thoma

[11] Patent Number: 6,020,167
[45] Date of Patent: Feb. 1, 2000

[54] COMPOSITION USED AS A THERAPEUTIC AGENT AGAINST CHRONIC VIRAL HEPATIC DISEASES

[75] Inventor: Hans Thoma, München, Germany

[73] Assignee: Medeva Holdings B.V., Amsterdam, Netherlands

[21] Appl. No.: 08/075,520

[22] PCT Filed: Dec. 19, 1991

[86] PCT No.: PCT/EP91/02460

§ 371 Date: Jan. 31, 1994

§ 102(e) Date: Jan. 31, 1994

[87] PCT Pub. No.: WO92/11368

PCT Pub. Date: Jul. 9, 1992

[30] Foreign Application Priority Data

Dec. 19, 1990 [EP] European Pat. Off. .............. 90124775

[51] Int. Cl.⁷ ........................... G01N 33/53; A61K 39/29
[52] U.S. Cl. ................. 435/69.3; 424/189.1; 424/225.1; 424/227.1; 424/226.1; 530/324
[58] Field of Search ........................ 435/69.3; 424/189.1, 424/225.1, 226.1, 227.1; 530/324

[56] References Cited

U.S. PATENT DOCUMENTS

| | | | |
|---|---|---|---|
| Re. 34,705 | 8/1994 | Galibert et al. ........................ | 530/329 |
| 3,636,191 | 1/1972 | Blumberg et al. . | |
| 4,415,491 | 11/1983 | Vyas ........................................ | 530/327 |
| 4,428,941 | 1/1984 | Galibert et al. ............................ | 514/2 |
| 4,563,423 | 1/1986 | Murray et al. . | |
| 4,599,230 | 7/1986 | Milich et al. ......................... | 424/189.1 |
| 4,599,231 | 7/1986 | Milich et al. ......................... | 424/189.1 |
| 4,639,271 | 1/1987 | Prince et al. . | |
| 4,649,192 | 3/1987 | Van Wijnendaele et al. .......... | 530/371 |
| 4,683,136 | 7/1987 | Milich et al. ............................... | 435/5 |
| 4,696,898 | 9/1987 | Fitts et al. ............................. | 435/172.3 |
| 4,710,463 | 12/1987 | Murray ................................... | 435/172.3 |
| 4,722,840 | 2/1988 | Valenzuela et al. .................. | 435/172.3 |
| 4,741,901 | 5/1988 | Levinson et al. ..................... | 435/240.2 |
| 4,742,158 | 5/1988 | Lehman et al. ......................... | 530/371 |

(List continued on next page.)

FOREIGN PATENT DOCUMENTS

| | | |
|---|---|---|
| 1093088 | 8/1988 | Australia . |
| 1094311 | 11/1994 | China . |
| 1108306 | 9/1995 | China . |
| 1109784 | 10/1995 | China . |
| 0013828 | 8/1980 | European Pat. Off. . |
| 0020251 | 12/1980 | European Pat. Off. . |
| 0 044 710 A1 | 1/1982 | European Pat. Off. . |
| 0 072 318 B1 | 2/1983 | European Pat. Off. . |
| 0 120 551 B1 | 10/1984 | European Pat. Off. . |
| 0 154 902 B1 | 9/1985 | European Pat. Off. . |
| 0154902 | 9/1985 | European Pat. Off. . |
| 0155146 | 9/1985 | European Pat. Off. . |
| 0155198 | 9/1985 | European Pat. Off. . |
| 0156712 | 10/1985 | European Pat. Off. . |
| 0 171 908 A2 | 2/1986 | European Pat. Off. . |

(List continued on next page.)

OTHER PUBLICATIONS

Alberts et al., *Molecular Biology of the Cell*, second edition, Garland Publishing Inc., New York and London, pp. 172–173 (1989).

Atassi, "Antigenic Structures of Proteins," *Eur. J. Biochem.*, 145:1–20 (1984).

Atassi et al., "Localization, Synthesis, and Activity of an Antigenic Site on Influenza Virus Hemagglutinin," *Proc. Natl. Acad. Sci. USA*, 80:840–844 (1983).

Baron et al., "Antibodies Against a Synthetic Peptide of the Poliovirus Replicase Protein: Reaction with Native, Virus–Encoded Proteins and Inhibition of Virus–Specific Polymerase Activities In Vitro," *Journal of Virology*, 43(3):969–978 (Sep. 1982).

Bittle et al., "Protection Against Foot–and–Mouth Disease by Immunization with a Chemically Synthesized Peptide Predicted from the Viral Nucleotide Sequence," *Nature*, 298:30–33 (Jul. 1, 1982).

Burrell et al., "Expression in *Escherichia coli* of Hepatitis B Virus DNA Sequences Cloned in Plasmid pBR322," *Nature*, 279:43–47 (May 3, 1979).

Dreesman et al., "Antibody to Hepatitis B Surface Antigen after a Single Inoculation of Uncoupled Synthetic HBsAg Peptides," *Nature*, 295:158–160 (Jan. 14, 1982).

Emtage et al, "The Production of Vaccines by Recombinant DNA Techniques," *New Developments With Human and Veterinary Vaccines*, pp. 367–409 (1980).

Fritsch et al., "Virology–Cloning the Genome of the Hepatitis B Virus in *E. Coli*," *C.R. Acad. Sci.*, Paris, 287:1453–1456 (Dec. 18, 1978).

Ganem, "Assembly of Hepadnaviral Virions and Subviral Particles," *Current Topics in Microbiology and Immunology*, 168:61–83 (1991).

Green et al., "Immunogenic Structure of the Influenza Virus Hemagglutinin," *Cell*, 28:477–487 (Mar. 1982).

Hemmerling et al., "Comparison of the Entire Pre–S Peptide Sequence to Selected Epitope Sequences in a New Hepatitis B Vaccine Development," International Symposium on Progress in Hepatitis B Immunization (May 3–5, 1989).

Hopp et al., "Prediction of Protein Antigenic Determinants from Amino Acid Sequences," *Proc. Natl. Acad. Sci. USA*, 78(6):3824–3828 (Jun. 1981).

Landers et al., "Structure of Hepatitis B Dane Particle DNA and Nature of the Endogenous DNA Polymerase Reaction," *Journal of Virology*, 23(2):368–376 (Aug. 1977).

Lenkei et al., "Receptors for Polymerized Albumin on Liver Cells," *Experientia*, 33:1046–1047 (1977).

(List continued on next page.)

Primary Examiner—Chris Eisenschenk
Assistant Examiner—Mary Zeman
Attorney, Agent, or Firm—Popovich & Wiles, P.A.

[57] ABSTRACT

A combination, comprising at least one polypeptide sequence, mediating the antigenicity of one or more epitopes, and a carrier, capable of presenting this/these polypeptide sequence(s), which are useful for the production of a medicament for the treatment of chronic viral hepatitis, is provided.

40 Claims, 12 Drawing Sheets

U.S. PATENT DOCUMENTS

| | | | |
|---|---|---|---|
| 4,758,507 | 7/1988 | Murray et al. | 435/5 |
| 4,777,240 | 10/1988 | Moriarty et al. | 530/326 |
| 4,816,564 | 3/1989 | Ellis et al. | 530/350 |
| 4,818,527 | 4/1989 | Thornton et al. | 424/189.1 |
| 4,847,080 | 7/1989 | Neurath et al. | 530/324 |
| 4,861,588 | 8/1989 | Neurath et al. | 530/324 |
| 4,882,145 | 11/1989 | Thornton et al. | 424/189.1 |
| 4,883,865 | 11/1989 | Kubek | 530/415 |
| 4,895,800 | 1/1990 | Tschopp et al. | 435/69.3 |
| 4,935,235 | 6/1990 | Rutter et al. | 424/189.1 |
| 4,942,125 | 7/1990 | Moriarty | 435/7.92 |
| 4,945,046 | 7/1990 | Horii et al. | 435/69.3 |
| 4,959,323 | 9/1990 | Acs et al. | 435/252.33 |
| 4,963,483 | 10/1990 | Ellis et al. | 435/69.3 |
| 4,977,092 | 12/1990 | Bitter | 435/320.1 |
| 5,011,915 | 4/1991 | Yamazaki | 530/414 |
| 5,024,938 | 6/1991 | Nozaki et al. | 435/68.1 |
| 5,039,522 | 8/1991 | Neurath | 424/194.1 |
| 5,068,185 | 11/1991 | Hopper et al. | 435/69.1 |
| 5,098,704 | 3/1992 | Valenzuela | 435/227.1 |
| 5,102,989 | 4/1992 | Sitrin et al. | 530/371 |
| 5,133,961 | 7/1992 | Ellis et al. | 424/189.1 |
| 5,143,726 | 9/1992 | Thornton et al. | 530/324 |
| 5,158,769 | 10/1992 | Neurath et al. | 424/189.1 |
| 5,196,194 | 3/1993 | Rutter et al. | 424/189.1 |
| 5,198,348 | 3/1993 | Bitter | 435/69.1 |
| 5,204,096 | 4/1993 | Neurath et al. | 424/189.1 |
| 5,242,812 | 9/1993 | Even-Chen | 435/70.3 |
| 5,314,808 | 5/1994 | Tiollais et al. | 435/69.3 |
| 5,324,513 | 6/1994 | Sobczak et al. | 424/227.1 |
| 5,436,139 | 7/1995 | Rutter et al. | 435/69.3 |
| 5,462,863 | 10/1995 | Hsieh et al. | 435/69.3 |
| 5,565,548 | 10/1996 | Neurath et al. | |
| 5,591,638 | 1/1997 | Tiollais et al. | 435/320.1 |
| 5,620,844 | 4/1997 | Neurath et al. | |
| 5,792,463 | 8/1998 | Valenzuela et al. | |
| 5,837,249 | 11/1998 | Heber-Katz et al. | |
| 5,840,303 | 11/1998 | Chrisari et al. | |

FOREIGN PATENT DOCUMENTS

| | | |
|---|---|---|
| 0 174 759 A1 | 3/1986 | European Pat. Off. |
| 0175261 | 3/1986 | European Pat. Off. |
| 0 182 442 B2 | 5/1986 | European Pat. Off. |
| 0180012 | 5/1986 | European Pat. Off. |
| 0 199 480 A2 | 10/1986 | European Pat. Off. |
| 0198474 | 10/1986 | European Pat. Off. |
| 0 201 416 B1 | 11/1986 | European Pat. Off. |
| 0 218 474 A2 | 4/1987 | European Pat. Off. |
| 0243913 | 11/1987 | European Pat. Off. |
| 0244924 | 11/1987 | European Pat. Off. |
| 0 248 410 A2 | 12/1987 | European Pat. Off. |
| 0250253 | 12/1987 | European Pat. Off. |
| 0251460 | 1/1988 | European Pat. Off. |
| 0257507 | 3/1988 | European Pat. Off. |
| 0 271 302 A2 | 6/1988 | European Pat. Off. |
| 0271302 | 6/1988 | European Pat. Off. |
| 0 278 940 A2 | 8/1988 | European Pat. Off. |
| 0 299 242 A2 | 1/1989 | European Pat. Off. |
| 0 300 213 A1 | 1/1989 | European Pat. Off. |
| 0304578 | 3/1989 | European Pat. Off. |
| 0 344 864 A2 | 12/1989 | European Pat. Off. |
| 0 344 864 A3 | 9/1990 | European Pat. Off. |
| 0385610 | 9/1990 | European Pat. Off. |
| 0 414 374 A2 | 2/1991 | European Pat. Off. |
| 0 421 626 A1 | 4/1991 | European Pat. Off. |
| 0 448 126 A1 | 9/1991 | European Pat. Off. |
| 0 491 077 A1 | 6/1992 | European Pat. Off. |
| 0 511 854 A1 | 11/1992 | European Pat. Off. |
| 0 511 855 A1 | 11/1992 | European Pat. Off. |
| 0 563 093 B1 | 8/1998 | European Pat. Off. |
| 58-194897 | 11/1983 | Japan. |
| 59-074985 | 4/1984 | Japan. |
| 59-080615 | 5/1984 | Japan. |
| 8301783 | 5/1983 | WIPO. |
| 8402534 | 7/1984 | WIPO. |
| WO 86/05189 | 9/1986 | WIPO. |
| 8810300 | 12/1988 | WIPO. |
| WO 92/11368 | 7/1992 | WIPO. |

OTHER PUBLICATIONS

Lerner et al., "Chemically Synthesized Peptides Predicted from the Nucleotide Sequence of the Hepatitis B Virus Genome Elicit Antibodies Reactive with the Native Envelope Protein of Dane Particles," *Proc. Natl. Acad. Sci. USA*, 78(6):3403–3407 (Jun. 1961).

Machida et al., "A Hepatitis B Surface Antigen Polypeptide (P31) with the Receptor for Polymerized Human as Well as Chimpanzee Albumins," *Gastroenterology*, 85:268–274 (1983).

Neurath at al., "Antibodies as Immunological Probes for Studying the Denaturation of HBsAg," *Journal of Medical Virology*, 6:309–322 (1980).

Neurath, "Chemical Synthesis of Hepatitis B Vaccine," *Recent Developments in Prophylactic Immunization*, vol. 12, Ed. Zuckermann, Kluwer Academic Publishers (1989).

Pasek et al., "Hepatitis B Virus Genes and their Expression in *E. Coli*," *Nature*, 282:575–579 (Dec. 6, 1979).

Peterson et al., "Partial Amino Acid Sequence of Two Major Component Polypeptides of Hepatitis B Surface Antigen," *Proc. Natl. Acad. Sci. USA*, 74(4):1530–1534 (Apr. 1977).

Playfair, "Immune Intervention," *New Trends in Vaccines*, vol. 1, Ed. I. M. Roitt, Academic Press, London, 1984, pp. 4–7.

Poma et al., "The Superior Immunogenicity of a Pre–S1 Containing HBV Vaccine Compared to a S–Vaccine in Comparative Clinical Trials," Pre–Print of Poster from the 1990 International Symposium on Viral Hepatitis and Liver Disease.

Stibbe et al., "Characterization of Pre–S Gene Products in Hepatitis B Surface Antigen," *Developments in Biological Standardization*, 54:33–43 (1983).

Stibbe et al., "Variable Protein Composition of Hepatitis B Surface Antigen from Different Donors," *Virology*, 123:436–442 (1982).

Thoma et al., "Does the Pre–S2 Have the Same Effect in Improving the HBV Immune Response Compared to Pre–S1?", Pre–Print of Paper Presented at the 1990 International Symposium on Viral Hepatitis and Liver Disease, Apr. 1990 in Houston, Texas.

Thoma et al., "Evaluation of Immune Response in a Third Generation Hepatitis B Vaccine Containing Pre–S Proteins in Comparative Trials," *Progress in Hepatitis B Immunization*, 194:35–42 (1990).

Thoma et al., "Improvement of the Hepatitis–B Immune Response Through Pre–S Incorporation with Specific Respect to Elderly," Pre–Print of Poster from the 1990 International Symposium on Viral Hepatitis and Liver Disease.

Thoma et al., "Recombinant Hepatitis B Particles Containing Pre–S1 and Pre–S2 as a Third Generation Hepatitis B Vaccine," International Conference, Current Trends in Chronically–Evolving Viral Hepatitis, Oct. 5–8, 1988, Fiuggi, Italy.

Thoma et al., "Third Generation Hepatitis B Vaccine Based on Variable Recombinanat Control of Amount of Pre–S, S, and Subtypes Secreted as Particles from Mammalian Cells," Reprint of Presentation from the II International Symposium on Viral Hepatitis and Hepatocellular Carcinoma, Dec. 1988, Taipei, Taiwan.

Tiollais et al, "Biology of Hepatitis B Virus," *Science*, 213:406–411 (Jul., 1981).

Valenzuela et al., "The Nucleotide Sequence of the Hepatitis B Viral Genome and the Identification of the Major Viral Genes," *Animal Virus Genetics*, pp. 57–70 (1980).

Villa–Komaroff et al., "A Bacterial Clone Synthesizing Proinsulin," *Proc. Natl. Acad. Sci. USA*, 75:3727–3731 (Aug. 1978).

Wands et al., "Immunodiagnosis of Hepatitis B by Epitope Binding with High–Affinity 1gM Monoclonal Antibodies," Viral Hepatitis 1981 International Symposium, Ed. Szmuness, Alter and Maynard, The Franklin Institute, pp. 707–708 (1982).

Zuckerman, "Developments with Hepatitis B Vaccines," *New Trends and Developments in Vaccines*, Ed. A. Voller and H. Friedman, MTP Press Limited, pp. 171–177 (1978).

Summons to Attend Oral Proceedings Pursuant to Rule 71(1) EPC, 5 pages, Nov. 27, 1997.

Opposition by Medeva PLC to European Patent No. 154 902 (New York Blood Center Inc. et al.), 14 pages, Feb. 1996.

Counterstatement by the Patentee, European Patent No. 154 902 (New York Blood Center et al.), pp. 1–22; Amended Claims (Main Request); Basis Schedule for Claims of the Main Request, pp. 1–5 (Oct. 1996).

Supplementary Counterstatement by the Patentee, European Patent No. 154 902 (New York Blood Center et al.) Apr. 17, 1998, including 5 pages of counterstatement, 19 pages of claims, and 1 page of cover letter.

May 26, 1999 Notice of Opposition to EP 0 563 093 B1 by SmithKline Beecham (2 pages), Memorandum of Opposition (22 pages), Annex 1 (6 pages), and Annex 2 (3 pages including cover sheet).

Brzosko et al., "Immunostimulation for Chronic Active Hepatitis," *Lancet*, 2 (8084):311 (1978).

Kassur et al., "Principles and theoretical considerations in the treatment of chronic hepatitis B with immunostimulation," *Pol Arch Med Wewn (Poland)*, 60(4):305–312 (1978).

Ferrari et al., "The preS1 Antigen of hepatitis B Virus is Highly Immunogenic at the T Cell Level in Man," *J. Clin. Invest*, 84:1314–1319 (1989).

Ferrari et al., "Cellular Immune Response to Hepatitis B Virus–Encoded Antigens in Acute and Chronic Hepatitis B Virus Infection," *J. Immunology*, 145:3442–3449 (1990).

"Viral Liver Disease," *Lancet*, 3:944–945 (Nov. 3, 1979).

Hong et al., "Seroconversion from HBsAg to antibody after allogeneic bone marrow transplantation," in *Viral Hepatitis and Hepatocellular Carcinoma*, Proceedings of the Second International Symposium on Viral Hepatitis and Hepatocellular Carcinoma, Taipei, Dec. 7–9, 1988, Excerpta Medica Asia Ltd., Hong Kong, pp. 201–205 (1990).

Welmar et al., "Prophylaxis and Therapy of HbsAg Positive Hepatitis," *Biomedicine*, 30:135–138 (1979).

Murray et al., "Protective Immunisation against Hepatitis B with an Internal Antigen of the Virus," *J. Med. Virol.*, 23:101–107 (1987).

Raimondo et al., "Interrupted Replication of Hepatitis B Virus in Liver Tissue of HbsAg Carriers with Hepatocelluar Carcinoma," *Virology*, 166:103–112 (1988).

Rehermann et al., "Differential cytotoxic T–lymphocyte responsiveness to the hepatitis B and C viruses in chronically infected patients," *J. Virol.*, 70 (10):7092–102 (Abstract only) (1996).

Adams et al., "The Expression of Hybrid HIV:TY Virus–like Particles in Yeast," *Nature*, 329:68–70 (Sep. 3, 1987).

Bruss et al., "Functions of the Internal Pre–S Domain of the Large Surface Protein in Hepatitis B Virus Particle Morphogenesis," *Journal of Virology*, 69(11):6652–6657 (1995).

Deepen et al., "Assay of PreS Epitopes and PreS1 Antibody in Hepatitis B Virus Carriers and Immune Persons," *Med. Microbiol. Immunol.*, 179:49–60 (1990).

Dehoux et al., "Expression of the Hepatitis B Virus Large Envelope Protein in *Saccharomyces Cerevisiae*," *Gene*, 48:155–163 (1986).

Delpeyroux et al., "Insertions in the Hepatitis B Surface Antigen Effect on Assembly and Secretion of 22–nm Particles from Mammalian Cells," *J. Mol. Biol.*, 195:343–350 (1987).

Delpeyroux et al., "Presentation and Immunogenicity of the Hepatitis B Surface Antigen and a Poliovirus Neutralization Antigen on Mixed Empty Envelope Particles," *Journal of Virology*, 62(5):1836–1839 (May 1988).

Dyson et al., "Selection of Peptide Inhibitors of Interactions Involved in Complex Protein Assemblies: Association of the Core and Surface Antigens of Hepatitis B Virus," *Proc. Natl. Acad. Sci. USA*, 92:2194–2198 (Mar. 1995).

Feitelson et al., "The Nature of Polypeptides Larger in Size than the Major Surface Antigen Components of Hepatitis B and Like Viruses in Ground Squirrels, Woodchucks, and Ducks," *Virology*, 130:76–90 (1983).

Francis et al., "Peptides with Added T–Cell Epitopes can Overcome Genetic Restriction of the Immune Response," *CSH*, pp. 9–13 (Sep. 1987) (abstract only).

Gallina et al., "A C–Terminal PreS1 Sequence is Sufficient to Retain Hepatitis B Virus L Protein in 293 Cells," *Virology*, 213:57–69 (1995).

Ganem et al., "The Molecular Biology of the Hepatitis B Viruses," *Ann. Rev. Biochem.*, 56:651–693 (1987).

Good et al., "Construction of Synthetic Immunogen: Use of New T–Helper Epitope on Malaria Circumsporozoite Protein," *Science*, 235:1059–1062 (Feb. 27, 1987).

Heermann et al., "Large Surface Proteins of Hepatitis B Virus Containing the Pre–S Sequence," *Journal of Virology*, 52(2):396–402 (Nov. 1984).

Heermann et al., "Immunogenicity of the Gene S and Pre–S Domains in Hepatitis B Virions and HBsAg Filaments," *Intervirology*, 28:14–25 (1987).

Lo et al., "Characterization of Restriction Endonuclease Maps of Hepatitis B Viral DNAs," *Biochemical and Biophysical Research Communications*, 129(3):797–803 (Jun. 28, 1985).

Machein et al., "Deletion and Insertion Mutants of HBsAg Particles," *Arch. Virology*, 4:133–136 (1992).

Najarian et al., "Primary Structure and Gene Organization of Human Hepatitis A Virus," *Proc. Nat'l. Acad. Sci.*, 82:2627–2631 (May 1985).

Neurath et al., "The Pre–S Region of Hepadnavirus Envelope Proteins," Academic Press, Inc., 34:65–142 (1988).

Persing et al., "The Pre S1 Protein of Hepatitis B Virus is Acylated at its Amino Terminus with Myristic Acid," *Journal of Virology*, pp. 1672–1677 (May 1987).

Pontisso et al., "Human Liver Plasma Membranes Contain Receptors for the Hepatitis B Virus Pre–S1 Region and, via Polymerized Human Serum Albumin, for the Pre–S2 Region," *Journal of Virology*, pp. 1981–1988 (May 1989).

Pontisso et al., "Identification of an Attachment Site for Human Liver Plasma Membranes on Hepatitis B Virus Particles," *Virology*, 173:522–530 (1989).

Prange et al., "Properties of Modified Hepatitis B Virus Surface Antigen Particles Carrying PreS Epitopes," *Journal of General Virology*, 76:2131–2140 (1995).

Stibbe et al., "Structural Relationships Between Minor and Major Proteins of Hepatitis B Surface Antigen," *Journal of Virology*, 46(2):626–628 (May 1983).

Summers et al., "Genome of Hepatitis B Virus: Restriction Enzyme Cleavage and Structure of DNA Extracted form Dane Particles," *Proc. Nat. Acad. Sci. USA*, 72(11):4597–4601 (Nov. 1975).

Valenzuela et al., "Antigen Engineering in Yeast: Synthesis and Assembly of Hybrid Hepatitis B Surface Antigen–herpes Simplex 1 gD Particles," *Bio/Technology*, 3:323–326 (Apr. 1985).

Valenzuela et al., "Synthesis and Assembly of Hepatitis B Virus Surface Antigen Particles in Yeast," *Nature*, 298:347–350 (Jul. 22, 1982).

Wampler et al., "Multiple Chemical Forms of Hepatitis B Surface Antigen Produced in Yeast," *Proc. Natl. Acad. Sci. USA*, 82:6830–6834 (Oct. 1985).

Waters et al., "A Study of the Antigenicity and Immunogenicity of a new Hepatitis B Vaccine Using a Panel of Monoclonal Antibodies," *DRAFT* (20 pages).

Wong et al., "Identification of Hepatitis B Virus Polypeptides Encoded by the Entire Pre–S Open Reading Frame," *Journal of Virology*, 55(1):223–231 (Jul. 1985).

Xu et al., "A Modified Hepatitis B Virus Surface Antigen with the Receptor–binding Site for Hepatocytes at its C Terminus: Expression, Antigenicity and Immunogenicity," *Journal of General Virology*, 75:3673–3677 (1994).

Zuckerman et al., "Immune Response to a New Hepatitis B Vaccine in Healthcare Workers who had not Responded to Standard Vaccine: Randomised Double Blind Dose–response Study," *BMJ*, 314:329–333 (Feb. 1, 1997).

Zuckerman et al., "Immunogenicity of a Novel Triple–S Hepatitis B Vaccine in Non–responder Healthcare Workers," *DRAFT* (22 pages).

Press Release, "Medeva PLC Announces New Positive Clinical Trial Results for Hepatitis B Product Hepagene as Vaccine and Treatment" (Oct. 16, 1997).

Dienstag et al., "Hepatitis B Vaccine Administered to Chronic Carriers of Hepatitis B Surface Antigen," *Annals of Internal Medicine*, 96(5):575–579 (1982).

Dusheiko et al., "Synthesis of Antibodies to Hepatitis B Virus by Cultured Lymphocytes from Chronic Hepatitis B Surface Antigen Carriers," *The Journal of Clinical Investigation*, 71:1104–1113 (May 1983).

Farci et al., "Lack of Protective Immunity Against Reinfection with Hepatitis C Virus," Science, 258:135–140 (Oct. 2, 1992).

Wilson et al., *Principles of Internal Medicine*, p. 1339 (1991).

Dubois et al., "Excretion of Hepatitis B Surface Antigen Particles from Mouse Cells Transformed with Cloned Viral DNA," *Proc. Natl. Acad. Sci. USA*, 77(8):4549–4553 (Aug. 1980).

Fattovich et al., "Cellular Immunity to the Hepatitis B Virion in Acute Hepatitis Type B," *Clin. Exp. Immunol.*, 53(3):645–650 (Sep. 1983).

Gerfaux et al., Constituents of HBs Particle: Characterization and Purity of HBsAg In <<HEVAC B>>, *Developments in Biological Standardization*, 54:45–52 (1983).

Haubitz et al., "Clinical Experience with a new Recombinant Hepatitis–B Vaccine in Previous Non–responders with Chronic Renal Insufficiency," *Clinical Nephrology*, 45(3):180–182 (1996).

Kent et al., "Approaches to a Totally Synthetic Vaccine for Hepatitis B Virus Based on Determinants Coded by the Pre–S Gene", *Peptide Chemistry 1984*, N. Izumiya (ed.), Protein Research Foundation, Osaka, Japan, 1985, 22:167–170.

Laub et al., "Synthesis of Hepatitis B Surface Antigen in Mammalian Cells: Expression of the Entire Gene and the Coding Region," *J. Virol.*, 48(1):271–280 (Oct. 1983).

McDermott et al., "HLA Haplotypes in Non–responders to Hepatitis B Vaccine and in Response to a Novel Recombinant Vaccine".

"Application for a Clinical Trial Exemption for Hep B–3 Hepatitis B Vaccine (rDNA)," Medeva Scientific and Regulatory Affairs (Sep. 1994).

Mishiro et al., "A 49,000–Dalton Polypeptide Bearing all Antigenic Determinants and Full Immunogenicity of 22–nm Hepatitis B Surface Antigen Particles," *Journal of Immunology*, 124(4):1589–1593 (Apr. 1980).

Offensperger et al., "Expression in *Escherichia Coli* of a Cloned DNA Sequence Encoding the Pre–S2 Region of Hepatitis B Virus," *Proc. Natl. Acad. Sci. USA*, 82(22):7540–7544 (Nov. 1985).

Pfaff et al., "Characterization of Large Surface Proteins of Hepatitis B Virus by Antiibodies to PreS–S Encoded Amino Acids," *Virology*, 148(1):15–22 (Jan. 15, 1986).

Wagner et al., "Hepatitis B Vaccination of Immunosuppressed Heart Transplant Recipients with the Vaccine Hepa Gene 3 Containing Pre–S1, Pre–S2, and S Gene Products," *The Clinical Investigator*, 72(5):350–353 (May 1994).

Bruss et al., "Functions of the Large Hepatitis B Virus Surface Protein in Viral Particle Morphogenesis," *Intervirology*, 39:23–31 (1996).

Gerhardt et al., "Phenotypic Mixing of Rodent but Not Avian Hepadnavirus Surface Proteins into Human Hepatitis B Virus Particles," *J. Virology*, 69(2):1201–1208 (Feb. 1995).

Hofmann et al., "Hepatocyte–Specific Binding of L/S–HBV Particles Expressed in Insect Cells," *Biol. Chem. Hoppe–Seyler*, 376:173–178 (Mar. 1995).

McDermott et al., "Hepatitis B Third Generation Vaccines: Improves Response and Conventional Vaccine Non–Response–Evidence for Genetic Basis in Man," *DRAFT*, pp. 1–7.

Melegari et al., "Properties of Hepatitis B Virus Pre–S1 Deletion Mutants," *Virology*, 199:292–300 (1994).

Milich et al., "Immune Response to the Pre–S(1) Region of the Hepatitis B Surface Antigen (HBsAg): A Pre–S(1)–Specific T–Cell Response can Bypass Nonresponsiveness to the Pre–S(2) and S Regions of HBsAg.," *J. Immunology*, 137(1):315–322 (Jul. 1, 1986).

Neurath et al., "Identification and Chemical Synthesis of a Host Cell Receptor Binding Site on Hepatitis B Virus," *Cell*, 46:429–436 (Aug. 1, 1986).

Petre et al., "Properties of a recombinant yeast–derived hepatitis B surface antigen containing S, preS2 and preS1 antigenic domains," *Arch. Virol.*, [Suppl] 4:137–141 (1992).

Sonveaux et al., "Characterization of the HBsAg particle lipid membrane," *Res. Virol.,* 146:43–51 (1995).

Wand et al., "Chronic Hepatitis", Chapter 23 in Harrison's *Principles of Internal Medicine,* 12$^{th}$ Edition, pp. 1337–1340 (1991).

Harrison's Principles of Internal Medicine 12th Edition, McGraw Hill, Publisher p. 1339, 1991.

V. Bruss and R. Thomssen, "Mapping a Region of the Large Envelope Protein Required for Hepatitis B Virion Maturation," Journal of Virology, vol. 68, No. 3, pp. 1643–1650 (1994).

Carloni et al., "A Transformed Vero Cell Line Stably Producing the Hepatitis B Virus Surface Antigen," Gene, vol. 31, pp. 49–57 (1984).

K. Cheng et al., "Hepatitis B Virus Large Surface Protein is Not Secreted but is Immunogenic When Selectively Expressed by Recombinant Vaccinia Virus," Journal of Virology, vol. 60, pp. 337–344 (1986).

B. E. Clarke et al., "Improved Immunogenicity of a Peptide Epitope After Fusion to Hepatitis B Core Protein," Nature, vol. 330, pp. 381–384 (1987).

Delpeyroux, "A Poliovirus Neutralization Epitope Expressed on Hybrid Hepatitis B Surface Antigen Particles," Science, vol. 233, pp. 472–475 (1986).

Fritsch et al., "Virologie," C.R. Academy of Sciences, pp. 1453–1456 (1978) (English abstract).

F. Galibert et al., "Nucleotide Sequence of the Hepatitis B Virus Genome (Subtype ayw) Cloned in *E. coli,*" Nature, vol. 281, pp. 646–650 (1979).

Hsiung et al., "Efficient Production of Hepatitis B Surface Antigen Using a Bovine Papilloma Virus–Metallothionein Vector," Journal of Molecular and Applied Genetics, vol. 2, pp. 497–506 (1984).

E. Jacobs et al., "Hepatitis B Recombinant Vaccines," Biotech International, pp. 349–354 (Jul. 1991).

W. N. Katkov et al., "Immunogenicity of a 'pre–S2 plus S' Hepatitis B Vaccine in Healthy Adults," Journal of Viral Hepatitis, vol. 1, pp. 79–83 (1994).

LeClerc et al., "A Synthetic Vaccine Constructed by Copolymerization of B and T Cell Determinants," European Journal of Immunology, vol. 17, pp. 269–273 (1987).

O. Marquardt et al., "Cell–Type Dependent Expression and Secretion of Hepatitis B Virus pre–S1 Surface Antigen," Postgraduate Medical Journal, vol. 63, Supp. 2, pp. 41–50 (1987).

W. J. McAleer et al., "Human Hepatitis B Vaccine from Recombinant Yeast," Nature, vol. 307, pp. 178–180 (1984).

M. Michel et al., "Synthesis in Animal Cells of Hepatitis B Surface Antigen Particles Carrying a Receptor for Polymerized Human Serum Albumin," Proc. Natl. Acad. Sci. USA, vol. 81, pp. 7708–7712 (1984).

D. R. Milich et al., "A Single 10–Residue Pre–S(1) Peptide Can Prime T Cell Help For Antibody Production to Multiple Epitopes Within the Pre–S(1), Pre–S(2), and S Regions of HBsAg,"Journal of Immunology, vol. 138, pp. 4457–4465 (1987).

Milich et al., "Immune Response to Hepatitis B Virus Core Antigen (HBcAg): Localization of T Cell Recognition Sites within HBcAg/HBeAg," Journal of Immunology, vol. 139, pp. 1223–1231 (1987).

Milich et al., "Nonoverlapping T and B Cell Determinants on an Hepatitis B Surface Antigen Pre–S(2) Region Synthetic Peptide," J. of Exp. Med., vol. 164, pp. 532–547 (1986).

Milich et al., "T Cell and B Cell Recognition of Native and Synthetic Pre–S Region Determinants on Hepatitis B Surface Agent," Vaccines, vol. 86, pp. 377–382 (1986).

Milich et al., "Two Distinct But Overlapping Anitbody Binding Sites in the Pre–S(2) Region of HBsAg Localized Within 11 Continuous Residues," Journal of Immunology, vol. 137, pp. 2703–2710 (1986).

Milich et al., Enhanced Immunogenicity of the Pre–S Region of Hepatitis B Surface Antigen, Science, vol. 228, 1195–1199 (1985).

E. Miskovsky et al., "Comparative Safety and Immunogenicity of Yeast Recombinant Hepatitis B Vaccines Containing S and pre–S2+S Antigens," Vaccine, vol. 9, pp. 346–350 (1991).

A. R. Neurath et al., "Hepatitis B Virus Surface Antigen (HBsAg) as Carrier for Synthetic Peptides Having an Attached Hydrophobic Tail," Molecular Immunology, vol. 26, pp. 53–62 (1989).

A. Neurath et al., "Hepatitis B Virus Contains pre–S Gene–Encoded Domains," Nature, vol. 315, pp. 154–156 (1985).

A. Neurath et al., "Location and Chemical Synthesis of a Pre–S Gene Coded Immunodominant Epitope of Hepatitis B Virus," Science, vol. 224, pp. 392–395 (1984).

Okamoto et al., "Nucleotide Sequence of a Cloned Hepatitis B Virus Genome, Subtype ayr: Comparison with Genomes of the Other Three Subtypes," Journal of General Virology, vol. 67, pp. 2305–2314 (1986).

Y. Ono et al., "The Complete Nucleotide Sequences of the Cloned Hepatitis B Virus DNA; Subtype adr and adw," Nucleic Acids Research, vol. 11, pp. 1747–1757 (1983).

Pavlakis et al., "Regulation of a Metallothionein–Growth Hormone Hybrid Gene in Bovine Papilloma Virus," Proc. Natl. Acad. Sci. USA, vol. 80, pp. 397–401 (1983).

D. H. Persing et al., "Inhibition of Secretion of Hepatitis B Surface Antigen by a Related Presurface Polypeptide," Science, vol. 234, pp. 1388–1391 (1986).

D. Persing et al., "A Frameshift Mutation in the pre–S Region of the Human Hepatitis B Virus Genome Allows Production of Surface Antigen Particles but Eliminates Binding to Polymerized Albumin," Proc. Natl. Acad. Sci. USA, vol. 82, pp. 3440–3444 (1985).

J. Pêtre et al., "Development of Hepatitis B Vaccine from Transformed Yeast Cells," Postgraduate Medical Journal, vol. 63, Supp. 2, pp. 73–81 (1987).

J. Pillot et al., "Weak Immunogenicity of the PreS2 Sequence and Lack of Circumventing Effect on the Unresponsiveness to the Hepatitis B Virus Vaccine," Vaccine, vol. 13, No. 3, pp. 289–294 (1995).

Rutgers et al., "Potential Future Recombinant Vaccines," in *Hepatitis B Vaccines in Clinical Practice,* R. W. Ellis, ed., Marcel Dekker, Inc., pp. 383–407 (1993).

D. Standring et al., "Assembly of Viral Particles in Xenopus Oocytes: Pre–Surface–Antigens Regulate Secretion of the Hepatitis B Viral Surface Envelope Particle," Proc. Natl. Acad. Sci. USA, vol. 83, pp. 9338–9342 (1986).

P. Valenzuela et al., "Nucleotide Sequence of the Gene Coding for the Major Protein of Hepatitis B Virus Surface Antigen," Nature, vol. 280, pp. 815–819 (1979).

P. Valenzuela et al., "Synthesis and Assembly in Yeast Of Hepatitis B Surface Antigen Particles Containing the Polyalbumin Receptor," Bio/Technology, vol. 3, pp. 317–320 (1985).

P. Winokur et al., "The Hepatitis A Virus Polyprotein Expressed by a Recombinant Vaccinia Virus Undergoes Protcolytic Processing and Assembly into Virus–like Particles," Journal of Virology, vol. 65, pp. 5029–5036 (1991).

Stibbe et al., "Structural Relationships Between Minor and Major Proteins of Hepatitis B Surface Antigen, "*Journal of Virology*, 46:626–628 (1983).

SEQUENCE LISTING (1) GENERAL INFORMATION:

(iii) NUMBER OF SEQUENCES: 40

(2) INFORMATION FOR SEQ ID NO: 1:

(i) SEQUENCE CHARACTERISTICS:
        (A) LENGTH: 558 bp
        (B) TYPE: Nucleic Acid
        (C) STRANDEDNESS: Single
        (D) TOPOLOGY: Linear (xi) SEQUENCE DESCRIPTION: SEQ ID NO: 1:

```
ATG GAC ATT GAC CCT TAT AAA GAA TTT GGA GCT ACT GTG GAG         42

TTA CTC TCG TTT TTG CCT TCT GAC TTC TTT CCT TCC GTA CGA         84

GAT CTC CTA GAC ACC GCC TCA GCT CTG TAT CGA GAA GCC TTA        126

GAG TCT CCT GAG CAT TGC TCA CCT CAC CAT ACT GCA CTC AGG        168

CAA GCC ATT CTC TGC TGG GGG GAA TTG ATG ACT CTA GCT ACC        210

TGG GTG GGT AAT AAT TTG CAA GAT CCA GCA TCC AGA GAT CTA        252

GTA GTC AAT TAT GTT AAT ACT AAC ATG GGT TTA AAG ATC AGG        294

CAA CTA TTG TGG TTT CAT ATA TCT TGC CTT ACT TTT GGA AGA        336

GAG ACT GTA CTT GAA TAT TTG GTC TCT TTC GGA GTG TGG ATT        378

CGC ACT CCT CCA GCC TAT AGA CCA CCA AAT GCC CCT ATG TTA        420

TCA ACA CTT CCG GAA ACT ACT GTT GTT AGA CGA CGG GAC CGA        462

GGC AGG TCC CCT AGA AGA AGA ACT CCC TCG CCT CGC AGA CGT        504
```

```
AGA TCT CAA TCG CCG CGT CGC AGA AGA TCT CAA TCT CGG GAA        546

TCT CAA TGT TAG                                                558
```

(2) INFORMATION FOR SEQ ID NO: 2:

(i) SEQUENCE CHARACTERISTICS:
        (A) LENGTH: 504 bp
        (B) TYPE: Nucleic Acid
        (C) STRANDEDNESS: Single
        (D) TOPOLOGY: Linear (xi) SEQUENCE DESCRIPTION: SEQ ID NO: 2:

```
ATG GAC ATT GAC CCT TAT AAA GAA TTT GGA GCT ACT GTG GAG         42

TTA CTC TCG TTT TTG CCT TCT GAC TTC TTT CCT TCC GTA CGA         84

GAT CTC CTA GAC ACC GCC TCA GCT CTG TAT CGA GAA GCC TTA        126

GAG TCT CCT GAG CAT TGC TCA CCT CAC CAT ACT GCA CTC AGG        168

CAA GCC ATT CTC TGC TGG GGG GAA TTG ATG ACT CTA GCT ACC        210

TGG GTG GGT AAT AAT TTG CAA GAT CCA GCA TCC AGA GAT CTA        252

GTA GTC AAT TAT GTT AAT ACT AAC ATG GGT TTA AAG ATC AGG        294

CAA CTA TTG TGG TTT CAT ATA TCT TGC CTT ACT TTT GGA AGA        336

GAG ACT GTA CTT GAA TAT TTG GTC TCT TTC GGA GTG TGG ATT        378

CGC ACT CCT CCA GCC TAT AGA CCA CCA AAT GCC CCT ATG TTA        420

TCA ACA CTT CCG GAA ACT ACT GTT GTT AGA CGA CGG GAC CGA        462

GGC AGG TCC CCT AGA AGA AGA ACT CCC TCG CCT CGA AGA CGT        504
```

(2) INFORMATION FOR SEQ ID NO: 3:

(i) SEQUENCE CHARACTERISTICS:
        (A) LENGTH: 504 bp
        (B) TYPE: Nucleic Acid
        (C) STRANDEDNESS: Single
        (D) TOPOLOGY: Linear (xi) SEQUENCE DESCRIPTION: SEQ ID NO: 3:

```
ATG GAC ATT GAC CCT TAT AAA GAA TTT GGA GCT ACT GTG GAG         42

TTA CTC TCG TTT TTG CCT TCT GAC TTC TTT CCT TCC GTA CGA         84

GAT CTC CTA GAC ACC GCC TCA GCT CTG TAT CGA GAA GCC TTA        126

GAG TCT CCT GAG CAT TGC TCA CCT CAC CAT ACT GCA CTC AGG        168

CAA GCC ATT CTC TGC TGG GGG GAA TTG ATG ACT CTA GCT ACC        210

TGG GTG GGT AAT AAT TTG CAA GAT CCA GCA TCC AGA GAT CTA        252

GTA GTC AAT TAT GTT AAT ACT AAC ATG GGT TTA AAG ATC AGG        294

CAA CTA TTG TGG TTT CAT ATA TCT TGC CTT ACT TTT GGA AGA        336

GAG ACT GTA CTT GAA TAT TTG GTC TCT TTC GGA GTG TGG ATT        378

CGC ACT CCT CCA GCC TAT AGA CCA CCA AAT GCC CCT ATG TTA        420

TCA ACA CTT CCG GAA ACT ACT GTT GTT AGA CGA CGG GAC CGA        462

GGC AGG TCC CCT AGA AGA AGA ACT CCC TCG CCT CGC AGA CGT        504
```

(2) INFORMATION FOR SEQ ID NO: 4:

(i) SEQUENCE CHARACTERISTICS:
        (A) LENGTH: 534 bp
        (B) TYPE: Nucleic Acid (C) STRANDEDNESS: Single
        (D) TOPOLOGY: Linear (xi) SEQUENCE DESCRIPTION: SEQ ID NO: 4:

TCC AAC CTG TGC CTT GGG TGG CTT TGG GGC ATG GAC ATT GAC         42

CCT TAT AAA GAA TTT GGA GCT ACT GTG GAG TTA CTC TCG TTT         84

TTG CCT TCT GAC TTC TTT CCT TCC GTA CGA GAT CTC CTA GAC        126

ACC GCC TCA GCT CTG TAT CGA GAA GCC TTA GAG TCT CCT GAG        168

CAT TGC TCA CCT CAC CAT ACT GCA CTC AGG CAA GCC ATT CTC        210

TGC TGG GGG GAA TTG ATG ACT CTA GCT ACC TGG GTG GGT AAT        252

AAT TTG CAA GAT CCA GCA TCC AGA GAT CTA GTA GTC AAT TAT        294

GTT AAT ACT AAC ATG GGT TTA AAG ATC AGG CAA CTA TTG TGG        336

TTT CAT ATA TCT TGC CTT ACT TTT GGA AGA GAG ACT GTA CTT        378

GAA TAT TTG GTC TCT TTC GGA GTG TGG ATT CGC ACT CCT CCA        420

GCC TAT AGA CCA CCA AAT GCC CCT ATG TTA TCA ACA CTT CCG        462

GAA ACT ACT GTT GTT AGA CGA CGG GAC CGA GGC AGG TCC CCT        504

AGA AGA AGA ACT CCC TCG CCT CGC AGA CGT                        534

(2) INFORMATION FOR SEQ ID NO: 5:

(i) SEQUENCE CHARACTERISTICS:
        (A) LENGTH: 534 bp
        (B) TYPE: Nucleic Acid
        (C) STRANDEDNESS: Single
        (D) TOPOLOGY: Linear (xi) SEQUENCE DESCRIPTION: SEQ ID NO: 5:

TCC AAC CTG TGC CTT GGG TGG CTT TGG GGC ATG GAC ATT GAC         42

CCT TAT AAA GAA TTT GGA GCT ACT GTG GAG TTA CTC TCG TTT         84

TTG CCT TCT GAC TTC TTT CCT TCC GTA CGA GAT CTC CTA GAC        126

ACC GCC TCA GCT CTG TAT CGA GAA GCC TTA GAG TCT CCT GAG        168

CAT TGC TCA CCT CAC CAT ACT GCA CTC AGG CAA GCC ATT CTC        210

TGC TGG GGG GAA TTG ATG ACT CTA GCT ACC TGG GTG GGT AAT        252

AAT TTG CAA GAT CCA GCA TCC AGA GAT CTA GTA GTC AAT TAT        294

GTT AAT ACT AAC ATG GGT TTA AAG ATC AGG CAA CTA TTG TGG        336

TTT CAT ATA TCT TGC CTT ACT TTT GGA AGA GAG ACT GTA CTT        378

GAA TAT TTG GTC TCT TTC GGA GTG TGG ATT CGC ACT CCT CCA        420

GCC TAT AGA CCA CCA AAT GCC CCT ATG TTA TCA ACA CTT CCG        462

GAA ACT ACT GTT GTT AGA CGA CGG GAC CGA GGC AGG TCC CCT        504

AGA AGA AGA ACT CCC TCG CCT CGC AGA CGT                        534

(2) INFORMATION FOR SEQ ID NO: 6:

(i) SEQUENCE CHARACTERISTICS:
        (A) LENGTH: 87 bp
        (B) TYPE: Nucleic Acid
        (C) STRANDEDNESS: Single
        (D) TOPOLOGY: Linear (xi) SEQUENCE DESCRIPTION: SEQ ID NO: 6:

| | |
|---|---|
| ATC CTC TGC TGG GGG GAA TGG ATG ACT CTA GCT ACC TGG GTG | 42 |
| GGC AAT AAT TTG GAA GAT CCA GCA TCT AGG GAC CTT GTA GTA | 84 |
| AAT | 87 |

(2) INFORMATION FOR SEQ ID NO: 7:

(i) SEQUENCE CHARACTERISTICS:
        (A) LENGTH: 81 bp
        (B) TYPE: Nucleic Acid
        (C) STRANDEDNESS: Single
        (D) TOPOLOGY: Linear (xi) SEQUENCE DESCRIPTION: SEQ ID NO: 7:

| | |
|---|---|
| GAC ATT GAC CCT TAT AAA GAA TTT GGA GCT ACT GTG GAG TTA | 42 |
| CTC TCG TTT TTG CCT TCT GAC TTC TTT CCT TCC GTC AGG | 81 |

(2) INFORMATION FOR SEQ ID NO: 8:

(i) SEQUENCE CHARACTERISTICS:
        (A) LENGTH: 114 bp
        (B) TYPE: Nucleic Acid
        (C) STRANDEDNESS: Single
        (D) TOPOLOGY: Linear (xi) SEQUENCE DESCRIPTION: SEQ ID NO: 8:

| | |
|---|---|
| TCC AAC CTG TGC CTT GGG TGG CTT TGG GGC ATG GAC ATT GAC | 42 |
| CCT TAT AAA GAA TTT GGA GCT ACT GTG GAG TTA CTC TCG TTT | 84 |
| TTG CCT TCT GAC TTC TTT CCT TCC GTC AGG | 114 |

(2) INFORMATION FOR SEQ ID NO: 9:

(i) SEQUENCE CHARACTERISTICS:
        (A) LENGTH: 90 bp
        (B) TYPE: Nucleic Acid
        (C) STRANDEDNESS: Single
        (D) TOPOLOGY: Linear (xi) SEQUENCE DESCRIPTION: SEQ ID NO: 9:

| | |
|---|---|
| GAT CTC CTA GAC ACC GCC TCA GCT CTG TAT CGA GAA GCC TTA | 42 |
| GAG TCT CCT GAG CTA TGC TCA CCT CAC CAT ACT GCA CTC AGG | 84 |
| CAA GGT | 90 |

(2) INFORMATION FOR SEQ ID NO: 10:

(i) SEQUENCE CHARACTERISTICS:
        (A) LENGTH: 261 bp
        (B) TYPE: Nucleic Acid
        (C) STRANDEDNESS: Single
        (D) TOPOLOGY: Linear (xi) SEQUENCE DESCRIPTION: SEQ ID NO: 10:

| | |
|---|---|
| ATG GAC ATT GAC CCT TAT AAA GAA TTT GGA GCT ACT GTG GAG | 42 |
| TTA CTC TCG TTT TTG CCT TCT GAC TTC TTT CCT TCC GTC AGG | 84 |
| GAT CTC CTA GAC ACC GCC TCA GCT CTG TAT CGA GAA GCC TTA | 126 |
| GAG TCT CCT GAG CTA TGC TCA CCT CAC CAT ACT GCA CTC AGG | 168 |
| CAA GGT ATC CTC TGC TGG GGG GAA TGG ATG ACT CTA GCT ACC | 210 |

```
TGG GTG GGC AAT AAT TTG GAA GAT CCA GCA TCT AGG GAC CTT           252

GTA GTA AAT                                                       261
```

(2) INFORMATION FOR SEQ ID NO: 11:

(i) SEQUENCE CHARACTERISTICS:
        (A) LENGTH: 291 bp
        (B) TYPE: Nucleic Acid
        (C) STRANDEDNESS: Single
        (D) TOPOLOGY: Linear (xi) SEQUENCE DESCRIPTION: SEQ ID NO: 11:

```
TCC AAC CTG TGC CTT GGG TGG CTT TGG GGC ATG GAC ATT GAC            42

CCT TAT AAA GAA TTT GGA GCT ACT GTG GAG TTA CTC TCG TTT            84

TTG CCT TCT GAC TTC TTT CCT TCC GTC AGG GAT CTC CTA GAC           126

ACC GCC TCA GCT CTG TAT CGA GAA GCC TTA GAG TCT CCT GAG           168

CTA TGC TCA CCT CAC CAT ACT GCA CTC AGG CAA GGT ATC CTC           210

TGC TGG GGG GAA TGG ATG ACT CTA GCT ACC TGG GTG GGC AAT           252

AAT TTG GAA GAT CCA GCA TCT AGG GAC CTT GTA GTA AAT               291
```

(2) INFORMATION FOR SEQ ID NO: 12:

(i) SEQUENCE CHARACTERISTICS:
        (A) LENGTH: 123 bp
        (B) TYPE: Nucleic Acid
        (C) STRANDEDNESS: Single
        (D) TOPOLOGY: Linear (xi) SEQUENCE DESCRIPTION: SEQ ID NO: 12:

```
ACC TGG GTG GGT AAT AAT TTG CAA GAT CCA GCA TCC AGA GAT            42

CTA GTA GTC AAT TAT GTT AAT ACT AAC ATG GGT TTA AAG ATC            84

AGG CAA CTA TTG TGG TTT CAT ATA TCT TGC CTT ACT TTT               123
```

(2) INFORMATION FOR SEQ ID NO: 13:

(i) SEQUENCE CHARACTERISTICS:
        (A) LENGTH: 138 bp
        (B) TYPE: Nucleic Acid
        (C) STRANDEDNESS: Single
        (D) TOPOLOGY: Linear (xi) SEQUENCE DESCRIPTION: SEQ ID NO: 13:

```
GCA TCC AGA GAT CTA GTA GTC AAT TAT GTT AAT ACT AAC ATG            42

GGT TTA AAG ATC AGG CAA CTA TTG TGG TTT CAT ATA TCT TGC            84

CTT ACT TTT GGA AGA GAG ACT GTA CTT GAA TAT TTG GTC TCT           126

TTC GGA GTG TGG                                                   138
```

(2) INFORMATION FOR SEQ ID NO: 14:

(i) SEQUENCE CHARACTERISTICS:
        (A) LENGTH: 822 bp
        (B) TYPE: Nucleic Acid
        (C) STRANDEDNESS: Single
        (D) TOPOLOGY: Linear (xi) SEQUENCE DESCRIPTION: SEQ ID NO: 14:

```
ATG CAG TGG AAT TCC AGA ACC TTC CAC CAA ACT CTG CAA GAT            42

CCC AGA GTG AGA GGC CTG TAT TTC CCT GCT GGT GGC TCC AGT            84
```

```
TCA GGA ACA GTA AAC CCT GTT CTG ACT ACT GCC TCT CCC TTA          126

TCG TCA ATC TTC TCG AGG ATA GAG AAC ATC ACA TCA GGA TTC          168

CTA GGA CCC CTT CTC GTG TTA CAG GCG GGG TTT TTC TTG TTG          210

ACA AGA ATC CTC ACA ATA CCG CAG AGT CTA GAC TCG TGG TGG          252

ACT TCT CTC AAT TTT CTA GGG GGA ACT ACC GTG TGT CTT GGC          294

CAA AAT TCG CAG TCC TCA ACC TCC AAT CAC TCA CCA ACC TCT          336

TGT CCT CCA ACT TGT CCT GGT TAT CGC TGG ATG TGT CTG CGG          378

CGT TTT ATC ATC TTC CTC TTC ATC CTG CTG CTA TGC CTC ATC          420

TTC TTG TTG GTT CTT CTG GAC TAT CAA GGT ATG TTG CCC GTT          462

TGT CCT CTA ATT CCA GGA TCC TCA ACA ACC AGC ACG GGA CCA          504

TGC CGG ACC TGC ATG ACT ACT GCT CAA GGA ACC TCT ATG TAT          546

CCC TCC TGT TGC TGT ACC AAA CCT TCG GAC GGA AAT TGC ACC          588

TGT ATT CCC ATC CCA TCA TCC TGG GCT TTC GGA AAA TTC CTA          630

TGG GAG TGG GCC TCA GCC CGT TTC TCC TGG CTC AGT TTA CTA          672

GTG CCA TTT GTT CAG TGG TTC GTA GGG CTT TCC CCC ACT GTT          714

TGG CTT TCA GTT ATA TGG ATG ATG TGG TAT TGG GGG CCA AGT          756

CTG TAC AGC ATC TTG AGT CCC TTT TTA CCG CTG TTA CCA ATT          798

TTC TTT TGT CTT TGG GTA TAC ATT                                 822

(2) INFORMATION FOR SEQ ID NO: 15:

(i) SEQUENCE CHARACTERISTICS:
        (A) LENGTH: 99 bp
        (B) TYPE: Nucleic Acid
        (C) STRANDEDNESS: Single
        (D) TOPOLOGY: Linear (xi) SEQUENCE DESCRIPTION: SEQ ID NO: 15:

TAT GTT AAT ACT AAC ATG GGT TTA AAG ATC AGG CAA CTA TTG          42

TGG TTT CAT ATA TCT TGC CTT ACT TTT GGA AGA GAG ACT GTA          84

CTT GAA TAT TTG GTC                                             99

(2) INFORMATION FOR SEQ ID NO: 16:

(i) SEQUENCE CHARACTERISTICS:
        (A) LENGTH: 390 bp
        (B) TYPE: Nucleic Acid
        (C) STRANDEDNESS: Single
        (D) TOPOLOGY: Linear (xi) SEQUENCE DESCRIPTION: SEQ ID NO: 16:

TCC AAC CTG TGC CTT GGG TGG CTT TGG GGC ATG GAC ATT GAC          42

CCT TAT AAA GAA TTT GGA GCT ACT GTG GAG TTA CTC TCG TTT          84

TTG CCT TCT GAC TTC TTT CCT TCC GTA CGA GAT CTC CTA GAC          126

ACC GCC TCA GCT CTG TAT CGA GAA GCC TTA GAG TCT CCT GAG          168

CAT TGC TCA CCT CAC CAT ACT GCA CTC AGG CAA GCC ATT CTC          210

TGC TGG GGG AAT TGA TGA CTA GCT ACC TGG GTG GGT AAT              252

AAT TTG CAA GAT CCA GCA TCC AGA GAT CTA GTA GTC AAT TAT          294

GTT AAT ACT AAC ATG GGT TTA AAG ATC AGG CAA CTA TTG TGG          336
```

```
TTT CAT ATA TCT GCT CTT ACT TTT GGA AGA GAG ACT GTA CTT        378

GAA TAT TTG GTC                                                 390
```

(2) INFORMATION FOR SEQ ID NO: 17:

(i) SEQUENCE CHARACTERISTICS:
        (A) LENGTH: 60 bp
        (B) TYPE: Nucleic Acid
        (C) STRANDEDNESS: Single
        (D) TOPOLOGY: Linear (xi) SEQUENCE DESCRIPTION: SEQ ID NO: 17:

```
AAT CCT CTG GGA TTC TTT CCC GAT CAC CAG TTG GAT CCA GCC         42

TTC AGA GCA AAC ACC GCA                                         60
```

(2) INFORMATION FOR SEQ ID NO: 18:

(i) SEQUENCE CHARACTERISTICS:
        (A) LENGTH: 63 bp
        (B) TYPE: Nucleic Acid
        (C) STRANDEDNESS: Single
        (D) TOPOLOGY: Linear (xi) SEQUENCE DESCRIPTION: SEQ ID NO: 18:

```
CCT GCC TCC ACC AAT CGC CAG TCA GGA AGG CAG CCT ACC CCG         42

CTG TCT CCA CCT TTG AGA AAC                                     63
```

(2) INFORMATION FOR SEQ ID NO: 19:

(i) SEQUENCE CHARACTERISTICS:
        (A) LENGTH: 63 bp
        (B) TYPE: Nucleic Acid
        (C) STRANDEDNESS: Single
        (D) TOPOLOGY: Linear (xi) SEQUENCE DESCRIPTION: SEQ ID NO: 19:

```
GAT CCA GCC TTC AGA GCA AAC ACC GCA AAT CCA GAT TGG GAC         42

TTC AAT CCC AAC AAG GAC ACC                                     63
```

(2) INFORMATION FOR SEQ ID NO: 20:

(i) SEQUENCE CHARACTERISTICS:
        (A) LENGTH: 108 bp
        (B) TYPE: Nucleic Acid
        (C) STRANDEDNESS: Single
        (D) TOPOLOGY: Linear (xi) SEQUENCE DESCRIPTION: SEQ ID NO: 20:

```
CCG CAC GGA GGC CTT TTG GGG TGG AGC CCT CAG GCT CAG GGC         42

ATA CTA CAA ACT TTG CCA GCA AAT CCG CCT CCT GCC TCC ACC         84

AAT CGC CAG TCA GGA AGG CAG CCT                                108
```

(2) INFORMATION FOR SEQ ID NO: 21:

(i) SEQUENCE CHARACTERISTICS:
        (A) LENGTH: 63 bp
        (B) TYPE: Nucleic Acid
        (C) STRANDEDNESS: Single
        (D) TOPOLOGY: Linear (xi) SEQUENCE DESCRIPTION: SEQ ID NO: 21:

CCT GCC TCC ACC AAT CGG CAG TCA GGA AGG CAG CCT ACT CCC        42

ATC TCT CCA CCT CTA AGA GAC                                    63

(2) INFORMATION FOR SEQ ID NO: 22:

(i) SEQUENCE CHARACTERISTICS:
        (A) LENGTH: 108 bp
        (B) TYPE: Nucleic Acid
        (C) STRANDEDNESS: Single
        (D) TOPOLOGY: Linear (xi) SEQUENCE DESCRIPTION: SEQ ID NO: 22:

CCA CAC GGC GGT ATT TTG GGG TGG AGC CCT CAG GCT CAG GGC        42

ATA TTG ACC ACA GTG TCA ACA ATT CCT CCT CCT GCC TCC ACC        84

AAT CGG CAG TCA GGA AGG CAG CCT                                108

(2) INFORMATION FOR SEQ ID NO: 23:

(i) SEQUENCE CHARACTERISTICS:
        (A) LENGTH: 60 bp
        (B) TYPE: Nucleic Acid
        (C) STRANDEDNESS: Single
        (D) TOPOLOGY: Linear (xi) SEQUENCE DESCRIPTION: SEQ ID NO: 23:

CAG TGG AAT TCC AGA ACC TTC CAC CAA ACT CTG CAA GAT CCC        42

AGA GTG AGA GGC CTG TAT                                        60

(2) INFORMATION FOR SEQ ID NO: 24:

(i) SEQUENCE CHARACTERISTICS:
        (A) LENGTH: 60 bp
        (B) TYPE: Nucleic Acid
        (C) STRANDEDNESS: Single
        (D) TOPOLOGY: Linear (xi) SEQUENCE DESCRIPTION: SEQ ID NO: 24:

GAT CCC AGA GTG AGA GGC CTG TAT TTC CCT GCT GGT GGC TCC        42

AGT TCA GGA ACA GTA AAC                                        60

(2) INFORMATION FOR SEQ ID NO: 25:

(i) SEQUENCE CHARACTERISTICS:
        (A) LENGTH: 558 bp
        (B) TYPE: Nucleic Acid
        (C) STRANDEDNESS: Single
        (D) TOPOLOGY: Linear (xi) SEQUENCE DESCRIPTION: SEQ ID NO: 25:

ATG GAC ATT GAC CCT TAT AAA GAA TTT GGA GCT ACT GTG GAG        42

TTA CTC TCG TTT TTG CCT TCT GAC TTC TTT CCT TCC GTA CGA        84

GAT CTC CTA GAC ACC GCC TCA GCT CTG TAT CGA GAA GCC TTA        126

GAG TCT CCT GAG CAT TGC TCA CCT CAC CAT ACT GCA CTC AGG        168

CAA GCC ATT CTC TGC TGG GGG GAA TTG ATG ACT CTA GCT ACC        210

TGG GTG GGT AAT AAT TTG CAA GAT CCA GCA TCC AGA GAT CTA        252

GTA GTC AAT TAT GTT AAT ACT AAC ATG GGT TTA AAG ATC AGG        294

CAA CTA TTG TGG TTT CAT ATA TCT GCC TTA ACT TTT GGA AGA        336

```
GAG ACT GTA CTT GAA TAT TTG GTC TCT TTC GGA GTG TGG ATT        378

CGC ACT CCT CCA GCC TAT AGA CCA CCA AAT GCC CCT ATG TTA        420

TCA ACA CTT CCG GAA ACT ACT GTT GTT AGA CGA CGG GAC CGA        462

GGC AGG TCC CCT AGA AGA AGA ACT CCC TCG CCT CGC AGA CGT        504

AGA TCT CAA TCG CCG CGT CGC AGA AGA TCT CAA TCT CGG AAA        546

TCT CAA TGT TAG                                                558

(2) INFORMATION FOR SEQ ID NO: 26:

(i) SEQUENCE CHARACTERISTICS:
        (A) LENGTH: 678 bp
        (B) TYPE: Nucleic Acid
        (C) STRANDEDNESS: Single
        (D) TOPOLOGY: Linear (xi) SEQUENCE DESCRIPTION: SEQ ID NO: 26:

ATA GAG AAC ATC ACA TCA GGA TTC CTA GGA CCC CTT CTC GTG         42

TTA CAG GCG GGG TTT TTC TTG TTG ACA AGA ATC CTC ACA ATA         84

CCG CAG AGT CTA GAC TCG TGG TGG ACT TCT CTC AAT TTT CTA        126

GGG GGA ACT ACC GTG TGT CTT GGC CAA AAT TCG CAG TCC TCA        168

ACC TCC AAT CAC TCA CCA ACC TCT TGT CCT CCA ACT TGT CCT        210

GGT TAT CGC TGG ATG TGT CTG CGG CGT TTT ATC ATC TTC CTC        252

TTC ATC CTG CTG CTA TGC CTC ATC TTC TTG TTG GTT CTT CTG        294

GAC TAT CAA GGT ATG TTG CCC GTT TGT CCT CTA ATT CCA GGA        336

TCC TCA ACA ACC AGC ACG GGA CCA TGC CGG ACC TGC ATG ACT        378

ACT GCT CAA GGA ACC TCT ATG TAT CCC TCC TGT TGC TGT ACC        420

AAA CCT TCG GAC GGA AAT TGC ACC TGT ATT CCC ATC CCA TCA        462

TCC TGG GCT TTC GGA AAA TTC CTA TGG GAG TGG GCC TCA GCC        504

CGT TTC TCC TGG CTC AGT TTA CTA GTG CCA TTT GTT CAG TGG        546

TTC GTA GGG CTT TCC CCC ACT GTT TGG CTT TCA GTT ATA TGG        588

ATG ATG TGG TAT TGG GGG CCA AGT CTG TAC AGC ATC TTG AGT        630

CCC TTT TTA CCG CTG TTA CCA ATT TTC TTT TGT CTT TGG GTA        672

TAC ATT                                                        678

(2) INFORMATION FOR SEQ ID NO: 27:

(i) SEQUENCE CHARACTERISTICS:
        (A) LENGTH: 585 bp
        (B) TYPE: Nucleic Acid
        (C) STRANDEDNESS: Single
        (D) TOPOLOGY: Linear (xi) SEQUENCE DESCRIPTION: SEQ ID NO: 27:

CTA GAC TCG TGG TGG ACT TCT CTC AAT TTT CTA GGG GGA TCT         42

CCC GTG TGT CTT GGC CAA AAT TCG CAG TCC CCA ACC TCC AAT         84

CAC TCA CCA ACC TCC TGT CCT CCA ATT TGT CCT GGT TAT CGC        126

TGG ATG TGT CTG CGG CGT TTT ATC ATA TTC CTC TTC ATC CTG        168

CTG CTA TGC CTC ATC TTC TTA TTG GTT CTT CTG GAT TAT CAA        210

GGT ATG TTG CCC GTT TGT CCT CTA ATT CCA GGA TCA ACA ACA        252
```

```
ACC AGT ACG GGA CCA TGC AAA ACC TGC ACG ACT CCT GCT CAA        294

GGC AAC TCT ATG TTT CCC TCA TGT TGC TGT ACA AAA CCT ACG        336

GAT GGA AAT TGC ACC TGT ATT CCC ATC CCA TCG TCC TGG GCT        378

TTC GCA AAA TAC CTA TGG GAG TGG GCC TCA GTC CGT TTC TCT        420

TGG CTC AGT TTA CTA GTG CCA TTT GTT CAG TGG TTC GTA GGG        462

CTT TCC CCC ACT GTT TGG CTT TCA GCT ATA TGG ATG ATG TGG        504

TAT TGG GGG CCA AGT CTG TAC AGC ATC GTG AGT CCC TTT ATA        546

CCG CTG TTA CCA ATT TTC TTT TGT CTC TGG GTA TAC ATT            585

(2) INFORMATION FOR SEQ ID NO: 28:

(i) SEQUENCE CHARACTERISTICS:
        (A) LENGTH: 106 bp
        (B) TYPE: Nucleic Acid
        (C) STRANDEDNESS: Single
        (D) TOPOLOGY: Linear (xi) SEQUENCE DESCRIPTION: SEQ ID NO: 28:

GAT CTT TAA CAT GGA GAA CAA TCC TCT GGG ATT CTT TCC CGA         42

TCA CCA GTT GGA TCC AGC CTT CAG AGC AAA CAC CGC AAA TCC         84

AGA TTG GGA CTT CAA TCC CAG T  106

(2) INFORMATION FOR SEQ ID NO: 29:

(i) SEQUENCE CHARACTERISTICS:
        (A) LENGTH: 115 bp
        (B) TYPE: Nucleic Acid
        (C) STRANDEDNESS: Single
        (D) TOPOLOGY: Linear (xi) SEQUENCE DESCRIPTION: SEQ ID NO: 29:

AAT TCT AGA CTC GAG TCT GAA CAT AGA GAA CAT CAC ATC AGG         42

ATT CCT AGG ACC CCT TCT CGT GTT ACA GGC GGG GTT TTT CTT         84

GTT GAC AAG AAT CCT CAC AAT ACC GCA GAG C                      115

(2) INFORMATION FOR SEQ ID NO: 30:

(i) SEQUENCE CHARACTERISTICS:
        (A) LENGTH: 108 bp
        (B) TYPE: Nucleic Acid
        (C) STRANDEDNESS: Single
        (D) TOPOLOGY: Linear (xi) SEQUENCE DESCRIPTION: SEQ ID NO: 30:

GAT CTT TTA AAG GGA TCC TCT GCT GGG GGG AAT GGA TGA CTC         42

TAG CTA CCT GGG TGG GCA ATA ATT TGG AAG ATC CAG CAT CTA         84

GGG ACC TTG TAG TAA ATC TAG ACA  108

(2) INFORMATION FOR SEQ ID NO: 31:

(i) SEQUENCE CHARACTERISTICS:
        (A) LENGTH: 106 bp
        (B) TYPE: Nucleic Acid
        (C) STRANDEDNESS: Single
        (D) TOPOLOGY: Linear (xi) SEQUENCE DESCRIPTION: SEQ ID NO: 31:

GAT CTC CGG GAA TTC CTG GGG CAT GGA CAT TGA CCC TTA TAA         42
```

```
AGA ATT TGG AGC TAC TGT GGA GTT ACT CTC GTT TTT GCC TTC        84

TGA CTT CTT TCC TTC CGT CAG G                                 106
```

(2) INFORMATION FOR SEQ ID NO: 32:

(i) SEQUENCE CHARACTERISTICS:
        (A) LENGTH: 89 bp
        (B) TYPE: Nucleic Acid
        (C) STRANDEDNESS: Single
        (D) TOPOLOGY: Linear (xi) SEQUENCE DESCRIPTION: SEQ ID NO: 32:

```
GAT CTC CTA GAC ACC GCC TCA GCT CTG TAT CGA GAA GCC TTA        42

GAG TCT CCT GAG CAT TGC TCA CCT CAC CAT ACT GCA CTC AGG        84

CAA GG                                                         89
```

(2) INFORMATION FOR SEQ ID NO: 33:

(i) SEQUENCE CHARACTERISTICS:
        (A) LENGTH: 25 bp
        (B) TYPE: Nucleic Acid
        (C) STRANDEDNESS: Single
        (D) TOPOLOGY: Linear (xi) SEQUENCE DESCRIPTION: SEQ ID NO: 33:

```
TTG GAT CCT CCA ACC TGT GCC TTG G                              25
```

(2) INFORMATION FOR SEQ ID NO: 34:

(i) SEQUENCE CHARACTERISTICS:
        (A) LENGTH: 25 bp
        (B) TYPE: Nucleic Acid
        (C) STRANDEDNESS: Single
        (D) TOPOLOGY: Linear (xi) SEQUENCE DESCRIPTION: SEQ ID NO: 34:

```
CCT CTA GAA CCA AAT ATT CAA GTA C                              25
```

(2) INFORMATION FOR SEQ ID NO: 35:

(i) SEQUENCE CHARACTERISTICS:
        (A) LENGTH: 588 bp
        (B) TYPE: Nucleic Acid
        (C) STRANDEDNESS: Single
        (D) TOPOLOGY: Linear (xi) SEQUENCE DESCRIPTION: SEQ ID NO: 35:

```
TCC AAC CTG TGC CTT GGG TGG CTT TGG GGC ATG GAC ATT GAC        42

CCT TAT AAA GAA TTT GGA GCT ACT GTG GAG TTA CTC TCG TTT        84

TTG CCT TCT GAC TTC TTT CCT TCC GTA CGA GAT CTC CTA GAC       126

ACC GCC TCA GCT CTG TAT CGA GAA GCC TTA GAG TCT CCT GAG       168

CAT TGC TCA CCT CAC CAT ACT GCA CTC AGG CAA GCC ATT CTC       210

TGC TGG GGG AAA TTG ATG ACT CTA GCT ACC TGG GTG GGT AAT       252

AAT TTG CAA GAT CCA GCA TCC AGA GAT CTA GTA GTC AAT TAT       294

GTT AAT ACT AAC ATG GGT TTA AAG ATC AGG CAA CTA TTG TGG       336

TTT CAT ATA TCT TGC CTT ACT TTT GGA AGA GAG ACT GTA CTT       378

GAA TAT TTG GTC TCT TTC GGA GTG TGG ATT CGC ACT CCT CCA       420

GCC TAT AGA CCA CCA AAT GCC CCT ATG TTA TCA ACA CTT CCG       462
```

```
GAA ACT ACT GTT GTT AGA CGA CGG GAC CGA GGC AGG TCC CCT            504

AGA AGA AGA ACT CCC TCG CCT CGC AGA CGT AGA TCT CAA TCG            546

CCG CGT CGC AGA AGA TCT CAA TCT CGG GAA TCT CAA TGT TAG            588

(2) INFORMATION FOR SEQ ID NO: 36:

(i) SEQUENCE CHARACTERISTICS:
        (A) LENGTH: 20 Amino Acids
        (B) TYPE: Amino Acid
        (D) TOPOLOGY: Linear (xi) SEQUENCE DESCRIPTION: SEQ ID NO: 36:

Asn Pro Leu Gly Phe Phe Pro Asp His Gln Leu Asp Pro Ala Phe
                 5                  10                  15

Arg Ala Asn Thr Ala
            20

(2) INFORMATION FOR SEQ ID NO: 37:

(i) SEQUENCE CHARACTERISTICS:
        (A) LENGTH: 21 Amino Acids
        (B) TYPE: Amino Acid
        (D) TOPOLOGY: Linear (xi) SEQUENCE DESCRIPTION: SEQ ID NO: 37:

Pro Ala Ser Thr Asn Arg Gln Ser Gly Arg Gln Pro Thr Pro Ile
                 5                  10                  15

Ser Pro Pro Leu Arg Asn
            20

(2) INFORMATION FOR SEQ ID NO: 38:

(i) SEQUENCE CHARACTERISTICS:
        (A) LENGTH: 21 Amino Acids
        (B) TYPE: Amino Acid
        (D) TOPOLOGY: Linear (xi) SEQUENCE DESCRIPTION: SEQ ID NO: 38:

Asp Pro Ala Phe Arg Ala Asn Thr Ala Asn Pro Asp Trp Asp Phe
                 5                  10                  15

Asn Pro Asn Lys Asp Thr
            20

(2) INFORMATION FOR SEQ ID NO: 39:

(i) SEQUENCE CHARACTERISTICS:
        (A) LENGTH: 36 Amino Acids
        (B) TYPE: Amino Acid
        (D) TOPOLOGY: Linear (xi) SEQUENCE DESCRIPTION: SEQ ID NO: 39:

Pro His Gly Gly Leu Leu Gly Trp Ser Pro Gln Ala Gln Gly Ile
                 5                  10                  15

Leu Glu Thr Leu Pro Ala Asn Pro Pro Ala Ser Thr Asn Arg
            20                  25                  30

Gln Ser Gly Arg Gln Pro
            35

(2) INFORMATION FOR SEQ ID NO: 40:

(i) SEQUENCE CHARACTERISTICS:
        (A) LENGTH: 36 Amino Acids
        (B) TYPE: Amino Acid
        (D) TOPOLOGY: Linear
```

-continued (xi) SEQUENCE DESCRIPTION: SEQ ID NO: 40:

Pro His Gly Gly Ile Leu Gly Trp Ser Pro Gln Ala Gln Gly Ile
                5                   10                  15

Leu Thr Thr Val Ser Thr Ile Pro Pro Pro Ala Ser Thr Asn Arg
                20                  25                  30

Gln Ser Gly Arg Gln Pro
                35

COMPOSITION USED AS A THERAPEUTIC AGENT AGAINST CHRONIC VIRAL HEPATIC DISEASES

This application is the National Stage of International Application No. PCT/EP91/02460, filed Dec. 19, 1991.

The present invention relates to a composition comprising a polypeptide sequence prepared by recombinant DNA techniques and a carrier to provide a curing agent against chronic viral hepatic diseases. The invention relates to DNA sequences coding for said polypeptide sequences and to transfected cells for the expression of the same.

At least five different viruses, namely Hepatitis virus A, B, C, D and E, are able to trigger the clinical aspect of an acute hepatitis. Hepatitis A and E, which are transferred enterically, always heal, whereas hepatitis B, C (formerly called parenteral hepatitis Non-A Non-B), and D can progress into a chronic stage of inflammation, which in turn can result in liver cirrhosis and primary hepatocellular carcinoma.

There is relatively little data available on hepatitis C and D, on methods for the diagnosis and their treatment and on the respective viruses. The hepatitis D virus is a RNA virus which is known to be incomplete. Therefore, it needs a helper virus to develop in patients and is found only in individuals infected with HBV. Only very recently the hepatitis C virus has been detected, and an antibody test (anti-HCV) facilitating the diagnosis of chronic hepatitis C infections has been developed. However, there is an increasingly urgent need for a treatment to cure this disease.

The same holds true for chronic hepatitis B, a much better studied disease with respect to its recognition by immunological methods, its causative virus and the viral life cycle and DNA sequence. Patients are said to be chronic carriers of the hepatitis B virus if the viral DNA persists longer than ten weeks, the HBe-antigen (HBeAg) for more than 12 weeks, or if the hepatitis B surface-antigen (HBsAg) is persistent longer than six months.

Roughly three hundred million people are deemed to suffer from chronic hepatitis B, most of them living in the Far East.

For these people the main risk to be infected appears to be during or immediately after birth, since a chronically infected mother transfers the virus to her newborn. 90 percent of the children infected this way will become chronically infected, too, during later life. In the Western World infection occurs more commonly later in life, during childhood or even adulthood, mainly by a parenteral or sexual transmission. In these cases of hepatitis B infection after birth only five to ten percent of the infected become chronic carriers. The virus transferred, however, is not responsible for distinct reactions shown by infected people either to eliminate the virus or to retain it in the body lifelong. Consequently, it seems to be a matter of the immunological status that determines the future physical condition.

The HB-virion (Dane particle) is composed of different structural proteins, the core proteins and the surface (S) proteins. The latter are translation products of an open reading frame encompassing the coding sequence of three S-type domains, each of which starts with an ATG triplet capable of initiating translation in vivo. The domains are referred to as preS1, preS2 and S in the order of 5' to the 3' end of the molecule. There are six protein products derived from this ORF: a glycosylated and a non-glycosylated form of the major protein (gp27 and p24) translated from the S domain only (226 amino acids), a middle protein (281 amino acids) having one or two polysaccharide side chains (gp33 and gp36, respectively), that is encoded by the preS2- and S-region, and finally, both a glycosylated (gp42) and a non-glycosylated (p39) form of the large protein (389–400 amino acids, depending upon the viral serotype), which is formed by translation of preS1, preS2 and S. The core proteins are HBcAg and HBeAg, the latter one conceivably being a processing product of HBcAg.

The Dane particle, which is the infectious virion, comprises both core and surface proteins, whereas the filaments consist of a mixture of the six surface antigens. The S peptides alone assemble to form the so-called 20 nm particles, which are completely uninfectious.

Patients infected by the HB virus pass through several stages of the hepatitis, before they are regarded to be chronically HBV-infected. Immediately after infection an infectious stage will follow, characterized by the presence of HBeAg in the serum. Continued HBs antigenaemia in spite of inhibited HBV replication indicates the presence of viral DNA sequences integrated into the cellular genome of the patient. The integrated viral sequences do not enable the host cell to synthesize the complete virus. However, liver cells having HBV-sequences integrated are capable of producing HBsAg only, which in turn is detectable in the serum of the patient and is an indicator for chronic hepatitis B. Most probably the transformed hepatocytes are not lysed by cytotoxic T-cells, but proliferate and induce either chronic persistent hepatitis (CPH) or chronic active hepatitis (CAH), which may then proceed to cirrhosis of the liver or to primary hepatocellular carcinoma resulting in premature death of the patient.

Recently it has been established that patients who are chronically HBV infected show a defect in endogenous interferon production (Abb et al., 1985: J. Med. Virol 16. 171–176). This was the rationale to treat patients suffering from chronic hepatitis B, as indicated by the presence of HBeAg and HBV-DNA in the serum, with interferon α (IFNα). Controlled trials with large numbers of patients showed that the administration of interferon α resulted in significantly increased elimination of the hepatitis B-virus, when compared to controls. However, persons infected at or around time of birth do not appear to seroconvert in response to this therapy. This phenomenon unfortunately precludes some 75% of carriers from IFNα therapy.

At present, the exact mode of action of interferon α on chronic hepatitis B remains unclear. Its antiviral activity might protect infected cells from infection or reduce viral transcription, translation and replication in HBV-infected cells. Interferon further has immunomodulatory effects by activating T-cells, macrophages and NK-cells and by inducing the expression of MHC class I proteins.

Another approach to treat chronic hepatitis B is based on the idea to inhibit replication of the virus, thus impairing its defence sufficiently to render the host immune system capable of eliminating the virus. This led to test antiviral drugs such as adenine arabinoside and adenine arabinoside monophosphate for treatment of chronically HBV infected individuals. However, less than half of the patients responded to this therapy, either by sustained or transient seroconversion (HBeAg$^+$ to anti-HBe$^+$). A further negative aspect of these antiviral drugs are their immunosuppressive properties.

Other drugs that have been tested for treatment of chronic carriers include interferon β and acycloguanosine (acyclovir), interleukin 2, steroids, such as prednisolone, and combinations thereof. But none of them could provide better results than treatment with interferon α. Only a combination therapy, including the initial administration of steroids followed by that of IFN α may increase the response rate in selected patients.

It is known from the prior art that chronically HBV infected chimpanzees can not be cured by treatment with HBsAg (bound to a tetanus toxoid) nor with anti-HBs antibodies. Furthermore, it has been attempted to immunize chronically HBV infected patients by administration of S peptides. This treatment did not even result in anti-HBs antibody formation in these persons.

Additionally, according to the definition, chronic carriers of hepatitis B virus are characterized in that HBsAg is detectable in their serum. Therefore, it has been absolutely unforeseeable, that a combination, comprising a T-cell activating epitope of the viral S peptide, according to the present invention, is able to induce an immunization in and a final healing of chronic carriers of hepatitis virus B.

Considering the above-discussed state of the art it is the objective of the present invention to provide an effective therapeutic agent for the treatment of viral chronic hepatic diseases which leads to a complete response (i.e. to the sustained inhibition of HBV-replication, the loss of HBV DNA and DNA polymerase and to a decrease and finally the disappearance of HBeAg and HBsAg in the serum of patients).

According to the present invention this goal is achieved by a combination of a) at least one polypeptide sequence mediating the antigenicity of one or more epitopes and b) a carrier, capable of presenting the epitope sequences) a), wherein the polypeptide sequence(s) a) can be bound to carrier b) by adsorption, any chemical bonding or secondary valences.

This invention is furthermore directed to the use of this combination for the production of a medicament for the treatment of chronic viral hepatitis.

The present invention is further directed to a method for the treatment of chronic viral hepatitis by administering to a patient the above described combination of a) at least one polypeptide sequence mediating the antigenicity of one or more epitopes and b) a carrier capable of presenting the epitope sequence(s) a), wherein the polypeptide sequence(s) a) can be bound to carrier b) by adsorption, any chemical bonding or secondary valences.

It is important that polypeptide sequence a), which may be one or more different polypeptides, mediates the antigenicity of a T cell-activating epitope in a direct or indirect way. According to the present invention polypeptide sequence(s) a) may be a polypeptide or a combination of two or more polypeptides of hepatitis B virus of any subtype, particularly adw, ayw, adr and ady. These peptides derived from hepatitis B virus may be HBV peptides preS1, preS2 or S or the HBV core antigens.

Useful as polypeptide sequences a) are furthermore any of the above-stated polypeptides or a combination of two or more polypeptides which are modified either by amino acid deletions, whereby at least one epitope comprising at least six consecutive amino acid residues must be preserved, or by adding further amino acids either at the N-terminus, the C-terminus or as insertions into the polypeptide sequence(s) a). In each of these cases it is essential, however, that the biologial activity is maintained.

Preferably, polypeptide sequence(s) a) is myristylated.

In order to display the appropriate pharmacological activity it is necessary that in the combination of the present invention polypeptide sequence(s) a) is presented on a carrier b). This carrier consists of a particular substance which for example may consist of particles of a hydrophobic polymer, of inorganic particles, or of particles of a polysaccharide. Preferably, carrier b) is a second polypeptide sequence which forms particles upon secretion, said particles having preferably a diameter of at least 10 nm.

It is preferred that the particle forming polypeptide sequence b) is a substantial part of or the complete amino acid sequence of a polypeptide which may be selected from HBV S peptide, HBV core antigen, HAV core antigen, HAV surface antigen, HIV surface antigen and HIV core antigen as well as the surface antigen of polio virus. Preferred as the particle-forming carrier b) is HBV S peptide and/or core peptide.

When used as the carrier sequence b) the above-stated polypeptides may be modified by arbitrary deletions of amino acids, by substitutions of one or more amino acids or by adding one or more amino acids either at the N-terminus, the C-terminus or by insertion of one or more amino acids into the polypeptide sequence b), provided that the particle-forming capacity is maintained. Preferably, polypeptide sequence b) is myristylated.

If the carrier b) is a polypeptide sequence, both sequences a) and b) may be linked via one or more of the following interactions: hydrophobic anchoring (mediated by myristic acid), disulfide bridge formation, or both sequences may be connected by a peptide bond to form a fusion peptide. In the latter case optionally a spacer sequence may be inserted between polypeptide sequence(s) a) and polypeptide sequence b), which spacer sequence is linked to both polypeptides via peptide bonds.

The present invention furthermore provides a recombinant DNA molecule coding for a combination, that is useful for production of a medicament to treat chronic viral hepatic diseases. The recombinant DNA molecule comprises at least one first DNA sequence, optionally a second, a third and/or a fourth DNA sequence wherein i) said at least one first DNA sequence codes for at least one polypeptide sequence a) as defined above, ii) said second DNA sequence codes for a polypeptide sequence b) according to the above definition of the particle forming peptide, iii) said third DNA sequence codes for a spacer sequence, and iv) said fourth DNA sequence codes for a selection marker, and wherein the DNA sequences are controlled by DNA elements essential for expression, and optionally have a common reading frame.

On account of the fact, that many amino acids are designated by more than one triplet, there exist several DNA sequences embraced by the present invention, which code for the above-defined peptide sequences a) and b).

Apart from this, the invention further embraces recombinant DNA molecules, which differ from the above-defined recombinant DNA molecules by the fact, that up to 30% of the nucleotides may be substituted.

A further object of the present application is to provide a host cell transfected with a recombinant DNA molecule coding for the above combination, which is useful for treatment of chronically HBV-infected patients. This host cell may be a mammalian, a yeast or a bacterial cell. For the purpose of this invention it is preferred, that this cell does not produce any human serum proteins or any primate serum proteins other than the polypeptide(s) being comprised within the above combination.

The term "HBV S peptide" as used herein refers to the peptide encoded by the entire S region of the HBV genome. The term "HBV pre-S2 peptide" as used herein refers to the peptide encoded by the entire pre-S2 and S regions of the HBV genome. The term "HBV pre-S1 peptide" as used herein refers to the polypeptide encoded by the entire pre-S1, pre-S2 and S regions of the HBV genome. The term "epitope" as used herein refers to a sequence of at least six consecutive amino acids encoded by the designated genome region (e.g. a "HBV pre-S2 epitope" refers to a sequence of at least six amino acids encoded by the pre-S2 region of the HBV genome). The term "T-cell epitope" as used herein refers to an epitope that interacts with receptors on the surface of T-cells to enhance or otherwise effect an immune response.

As used herein "antigenicity" means the ability to provoke an immune response (e.g. acting as an antigen), the ability to cause the production of antibodies (e.g. acting as an antigen) and/or the ability to interact with a cell surface receptor so as to enhance an immune response or production of antibodies.

The term "HBV" means any subtype of the virus, particularly adw, ayw, adr and ayr, described in the literature (P. Valenzuela, Nature Vol. 280, p. 815 (1979), Gerlich, EP-A-85 111 361, Neurath, EP-A-85 102 250). Examples of peptide sequences thereof, constituting polypeptide sequence(s) a), which mediate the antigenicity of one or more epitopes, are shown in the Sequence Listing (SEQ ID No. 17–20, 22).

Preferred embodiments of the present invention are the following combinations:

HB S-antigen particles with specific epitopes (determinants) of the pre-S1-, pre-S2-, and/or core peptides;

HB core-antigen particles with specific epitopes (determinants) of the pre-S1-, pre-S2-, S-peptide, and/or of the core antigens;

Hepatitis A-antigen particles with specific epitopes (determinants) of the hepatitis B S,pre-S-1-, pre-S2-, and/or core-peptides.

Recombinant DNA molecules preferred for the present invention are characterized by the presence of sequences coding for polypeptide sequence(s) a), mediating the antigenicity of one or more T-cell epitopes, and for polypeptide b), which upon secretion forms particles having a diameter of 10 nm or more, both of which are under control of a suitable promoter. As examples for sequences coding for a) there may be mentioned any of the sequences listed under ID numbers 1 to 24 in the Sequence Listing. Examples for the DNA sequence coding for polypeptide sequence b) are represented by any of the ID-sequences 25 to 27 in the Sequence Listing.

Any of the 24 sequences (ID numbers 1 to 24) may be combined to any sequence disclosed under ID number 25 to 27 in the Sequence Listing, therein both orders a-b and b-a are included.

A particular preferred embodiment of the present invention consists in a combination of the epitope sequence ID No. 28 (corresponding to amino acids 9 to 28 of the S1 sequence of HBV) in combination with sequence ID No. 26 and/or 27 as a particle former.

Hepatitis virus sequences used in the recombinant DNA construct of the present invention can be formed or isolated by any means including isolation and ligation of restriction fragments, chemical synthesis of oligonucleotides using a synthesizer (Cyclon, BioSearch), and synthesis by the PCR method (T. J. White, N. Arnleim, H. E. Erlich, 1989; The Polymerase Chain Reaction, Technical Focus 5 (6)).

Preferred recombinant DNA molecules were formed by the ligation of synthetic oligonucleotides to a 5' XbaI-BglII 3' fragment (ID number 27) from the S region of the HBV genome, which is derived from a BglII-BglII HBV fragment including the entire pre-S1-pre-S2-S-region, or to the entire S-region. Oligonucleotides used in making such constructs are summarized in Table I below.

TABLE I

| Function | Definition | | SEQ ID No. |
|---|---|---|---|
| core (adw) | aa* | 59–87 | 6 |
| core (adw) | aa | 2–28 | 7 |
| core (adw) | aa | −10–28 | 8 |
| core (adw) | aa | 29–58 | 9 |
| core (adw) | aa | 1–87 | 10 |
| core (adw) | aa | −10–87 | 11 |
| core (adw) | aa | 70–110 | 12 |
| core (adw) | aa | 80–125 | 13 |
| core (adw) | aa | 88–120 | 15 |
| S1 (ayw) | aa | 9–28 | 17 |
| S1 (ayw) | aa | 83–103 | 18 |
| S1 (ayw) | aa | 20–40 | 19 |
| S1 (ayw) | aa | 59–94 | 20 |
| S1 (adw) | aa | 94–114 | 21 |
| S1 (adw) | aa | 70–105 | 22 |
| S2 (ayw) | aa | 2–21 | 23 |
| S2 (ayw) | aa | 14–33 | 24 |

*aa = amino acid

Other preferred DNA molecules were formed by ligation of core sequences, which are prepared by the PCR method and which code for T-cell epitopes, to the core sequence of HBV (SEQ ID NO 25) functioning as polypeptide sequence b). Oligonucleotides used in preparing these constructs are given in Table II-1.

TABLE II-1

| Function | Definition | SEQ ID No. |
|---|---|---|
| core | complete, bp 1901–2500 | 1 |
| core | C-terminal deletion, bp 1901–2405 | 2 |
| core | C-terminal deletion and stop codon inserted, bp 1901–2405 | 3 |
| core/precore | 10 aa precore, C-terminal deletion, bp 1871–2405 | 4 |
| core/precore | 10 aa precore, C-terminal deletion and stop codon inserted, bp 1871–2405 | 5 |
| core | aa (−10–120) | 16 |
| core/precore | 10 aa precore, complete core, bp 1871–2500 | 35 |

Table II-2 shows several examples, where the T-cell epitope-coding DNA sequences have been isolated by restriction fragmentation of the HBV genome and have been ligated to the DNA sequence coding for polypeptide sequence b) as defined above.

TABLE II–2

| Function | Definition | SEQ ID No. |
|---|---|---|
| core/precore | complete, bp 1403–31 | ** |
| S2 ay/ad | | ** |

TABLE II–2-continued

| Function | Definition | SEQ ID No. |
|---|---|---|
| S2 (K) ay/ad | S2–S, 7 codons deleted, start codon ATG changed to ATA | 14 |

**Sequence has been published by Galibert, F. et al. (1979: Nature 261, 646–650) and by Ono, Y. et al. (1983: Nucl. Acid Res. 11(6), 1747–1757)

In Table II-3 specific recombinant DNA molecules are listed. The procedure for their construction will be described in more detail in the Examples.

TABLE II-3

| Final construct | T-cell epitope | Particle Former | Selection Gene |
|---|---|---|---|
| MT-core(−10–120) + SAg + neo | core(aa −10–120) | S adw/ayw or S/XbaI/BglII | neo |
| MT-S1(aa 9–28)-S + egpt | S1(aa 9–28)ay | S adw/ayw or S/XbaI/BglII | egpt# |
| MT-core-neo | core/precore bp 1403–31 | core adw | neo |
| MT-core(1–87) + HBsAg - neo | core(aa 1–87) | S adw/ayw or s/XbaI/BglII | neo | egpt = *E coli* xanthine guanine phosphoribosyl transferase

Preferred recombinant DNA molecules according to the present invention comprise, apart from the regions coding for polypeptides a) and b), an additional DNA sequence coding for a selection marker. Furthermore, they comprise all usual elements essential for the expression, such as promoter sequence, start codon and a polyadenylation signal.

Examples of suitable promoters are the methallothionein (MT), the U2 and the H2K promoter in case of using mammalian cells as a host cell. If yeast or bacterial cells are to be employed, appropriate yeast and bacterial promoters, such as the GCN4- and the GAL 1/10 promoter or the prokaryotic trp- and tac promoters, respectively, may be used.

In order to produce the combination of polypeptide(s) a) and polypeptide b) according to this application the recombinant DNA molecule is inserted into host cells by transfection (in case of mammalian cells), by transformation (in case of yeast and bacterial cells), or by other means. As a host cells of any organism may be used that are capable of transcribing and translating recombinant DNA molecules, such as mammalian, bacterial and yeast cells.

Suitable mammalian cells according to this invention are for example VERO cells (a monkey kidney cell line), 3T3-, C127 and L cells (murine fibroblast cell lines), and CHO (Chinese hamster ovary) cells, which are either positive or negative in dehydrofolate reductase.

According to a specific embodiment of the present invention it is furthermore possible that the above-defined first DNA sequence and the above-defined second DNA sequence, which code for polypeptide sequence(s) a) and for a polypeptide sequence b), respectively, are present in different recombinant DNA molecules, in which case the host cells are cotransfected with both of these recombinant DNA molecules.

TABLE III

Possible alternatives of compositions for particles containing T-cell epitopes for targeting chronic h TABLE III-continued Possible alternatives of compositions for particles containing T-cell epitopes for targeting chronic hepatitis carrier

| | FINAL CONSTRUCT[1] | PROMOTER[2] | T-CELL-EPITOPE SYN | T-CELL-EPITOPE PCR | T-CELL-EPITOPE GENE | PARTICLE FORMER | SELECTION GENE | PURIFICATION |
|---|---|---|---|---|---|---|---|---|
| 3 | | MT/H2/U2 | | Core without pre-Core; with deletion at the C-terminus a stop signal e.g. bp 1901–2405 | | Core (adw) | neo/egpt | Materials and Methods |
| 4 | MT-core-neo | MT/H2/U2 | | Core and pre signal 10 AA | Core with pre-core i.e. bp 1403–31 | Core (adw) | neo/egpt | |
| 5 | | MT/H2/U2 | | Core and pre-core 10 AA; with deletion at the C-terminus e.g. bp 1871–2405 | | Core (adw) | neo/egpt | |
| 6 | | MT/H2/U2 | | Core and pre-core with deletion at the C-terminus + stop signal e.g. bp 1871–2405 | | Core (adw) | neo/egpt | |
| 7 | | MT/H2/U2 | Core (AA 59–87) | | | entire S adw/ayw S/XbaI/BglII | neo/egpt | |
| 8 | | MT/H2/U2 | Core (AA 2–28) | | | entire S adw/ayw S/XbaI/BglII | neo/egpt | |
| 9 | | MT/H2/U2 | Core (AA-10–+28) | | | entire S adw/ayw S/XbaI/BglII | neo/egpt | |
| 10 | | MT/H2/U2 | Core (AA 29–58) | | | entire S adw/ayw S/XbaI/BglII | neo/egpt | |
| 11 | MI-core (1–87) + HBsAg-neo | MT/H2/U2 | Core (AA 1–87) | | | entire S adw/ayw S/baI/BglII | neo/egpt | |

Notes: 1: see example 3
2: any of the stated promoters is suitable
3: see examples Table III gives an overview on how to combine suitable DNA sequences to get DNA constructs according to the present invention. It is to be noted that any constituents disclosed in this table may be combined to provide a DNA sequence which may be taken, if transfected into a host cell, to produce a combination (comprising polypeptides(s) a) and b)) as a medicament for the treatment of chronic viral hepatitis. The DNA sequences coding for the T-cell epitope sequences have been prepared synthetically (SYN) with a Biosearch Cyclon synthesizer, by PCR procedure (PCR), or by restriction enzyme fragmentation of the viral genome (GENE).

For the treatment of patients suffering from chronic viral hepatitis the combination of polypeptide sequence(s) a) and a carrier b) may be formulated in any type of a pharmaceutical composition, which furthermore comprises a suitable diluent or pharmaceutical carrier material, such as a buffer solution.

The administration may be effected by any method, i.e. by parenteral (e.g. intravenous or intramuscular) or oral (e.g. by using typhoid bacterial cells to encapsulate the active substance) administration.

The pharmaceutical preparation comprises the above-described combination in sufficient concentration to elicit a response upon administration.

Figure 1:
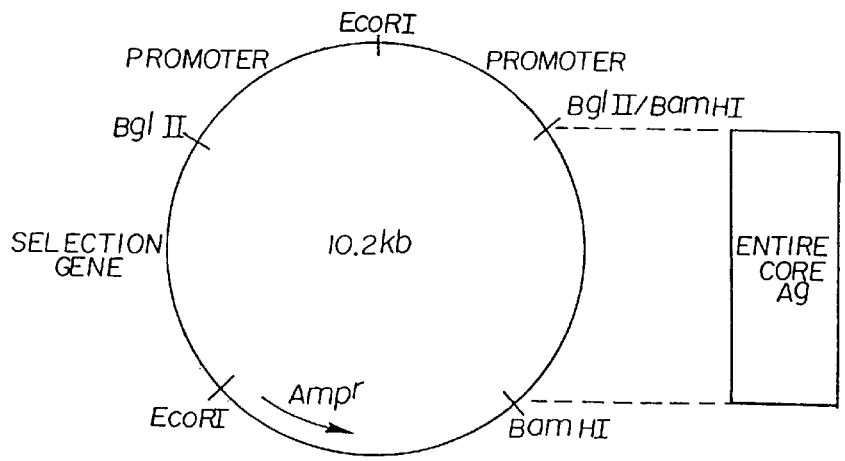
FIG. 1 shows a DNA construct, coding for a promoter, a particle former sequence and a selection gene (described in Example 3/4).
Figure 2:
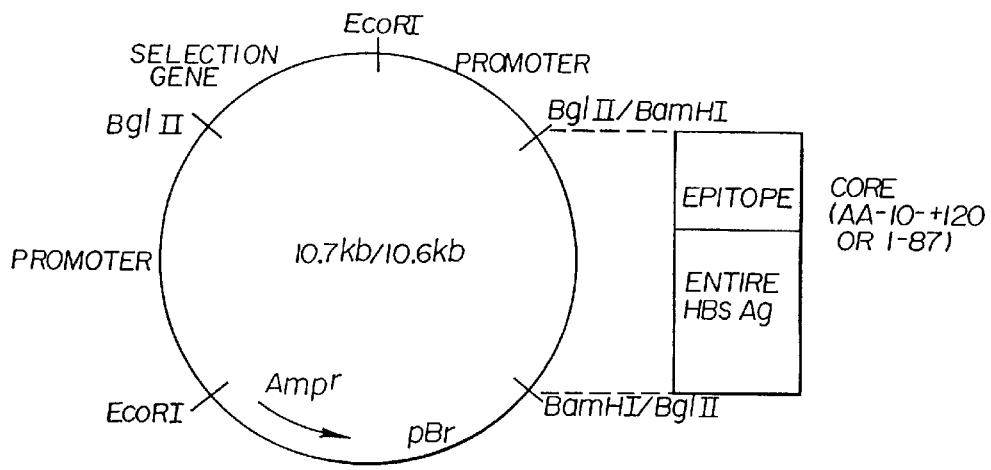
FIG. 2 shows a DNA-gene construct containing a promoter, an epitope with the entire HB-S-Ag and a selection gene (described in Example 3/18).
Figure 3:
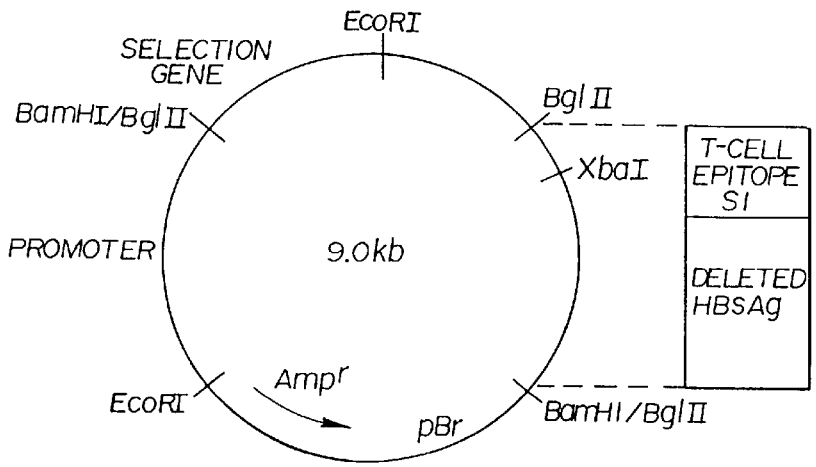
FIG. 3 shows a DNA construct presenting a promoter, a T-cell epitope with a particle former residue and a selection gene (described in Example 3/21).

The invention is more specifically described by the following examples.

EXAMPLE 1

1. Fractionated Precipitation With Polyethylene Glycol (PEG)

The supernatant of HBV protein producing cultures was collected and split into portions of 2,400 ml. To each portion 144 g of PEG 6000 (Serva) were added and dissolved by stirring at room temperature for 20 minutes and was stirred for another 6 hours at 4° C. The precipitate was separated by centrifugation in 500 ml bottles in a GS 3 rotor at 9,000 rpm (15,000×g) for 30 minutes at 10° C. The supernatant was collected and 144 g of PEG 6000 were added and dissolved as described above. The solution was stirred at 4° C. for 3 hours. The precipitate from this solution was harvested as described above except that centrifugation was continued for 60 minutes.

2. Gel Chromatography

The material obtained after PEG precipitation was redissolved in 20 ml PBS and submitted to gel chromatography on A-5 m (BioRad). Column dimensions were 25×1000 mm and 480 ml bed volume. In a typical fractionation run 1,000 µg of PEG precipitated HBV protein in 10 to 15 ml was loaded and eluted with PBS at a speed of 6 drops/min (18 ml/h). 3 ml fractions were collected. HBV protein eluted with the first peak. Collected fractions were submitted to a CsCl gradient.

3. Sedimentation in CsCl Gradient

About 30 fractions covering the first peak in column chromatography on A-5 m and containing prepurified HBV protein were collected to approximately 100 ml. This solution was adjusted to a density of 1.30 g/cc with CsCl and subsequently transferred to a polyallomer tube fitting into a SW 27/28 rotor (Beckman). A gradient was set by underlaying 4 ml of a CsCl solution of 1.35 g/cc and by overlaying 4 ml of 1.25 g/cc followed by 4 ml of 1.20 g/cc density. This gradient had been run at 28,000 rpm for 50 hours at 10° C. Thereafter the gradient was fractionated, and purified HBV protein floating in the 1.20 g/cc density layer was collected. The solution was desalted by three cycles of dialysis in bags against water.

EXAMPLE 2

Quantitative Determination of HBV Protein 1. with Radioimmunoassay

In the AUSRIA II-125 "sandwich" radioimmunoassay (commercially available from Abbot), beads coated with guinea pig antibody to Hepatitis B surface antigen (Anti-HBs) were incubated with serum or plasma or purified protein and appropriate controls. Any HBsAg present was bound to the solid phase antibody. After aspiration of the unbound material and washing of the bead, human 125T-Anti-HBs was allowed to react with the antibody-antigen complex on the bead. The beads were then washed to remove unbound $^{125}$I-Anti-HBs.

)-Anti-HBs HBsAg
)-Anti-HBs.HBsAg $^{125}$I-Anti-HBs
)-Anti-HBs.HBsAg.$^{125}$I-Anti-HBs The radioactivity remaining on the beads was counted in a gamma scintillation counter.

2. with ELISA

In the Enzygnost HBsAg micro "sandwich" assay (commercially available from Behring), wells were coated with anti-HBs. Serum plasma or purified protein and appropriate controls were added to the wells and incubated. After washing, peroxidase-labelled antibodies to HBsAg were reacted with the remaining antigenic determinants. The unbound enzyme-linked antibodies are removed by washing and the enzyme activity on the solid phase was determined. The enzymatically catalyzed reaction of hydrogen peroxide and chromogen was stopped by adding diluted sulfuric acid. The colour intensity was proportional to the HBsAg concentration of the sample and was obtained by photometric comparison of the colour intensity of the unknown samples

EXAMPLE 3

Preparation of gene constructs of the present invention containing promoter, desired antigen sequences and selection gene.

1. Isolation of the MT-promoter

The plasmid pBPV-342-12 (ATCC 37224) was digested with the endonucleases BglII and BamHI. Three DNA molecules were generated. The fragment of interest contains the methallothionein promoter and a pBR322 sequence comprising 4.5 kb and is easily detectable from the other fragments (2.0 kb and 7.6 kb).

The reaction was performed in a total volume of 200 μl of reaction buffer at a final concentration of 0.5 μg/μl DNA including 100 units of each restriction enzyme. The completion of the digestion was checked after incubation at 37° C. for three hours by agarose gel electrophoresis at a 0.8% agarose gel. The reaction was stopped by adding 4 μl 0.5 M EDTA.

The 4.5 kb fragment was separated from the other fragments by preparative 1.2% agarose gel electrophoresis. The DNA was eluted from the agarose gel on DE-81 Whatman filter paper from which the DNA was removed in a high salt buffer. The DNA was purified by a phenol-chloroform extraction and two ethanol precipitations.

2. Ligation of a 1.8 kb Fragment Coding for the HBV-core-antigen

A 1.8 kb BamHI-BamHI fragment, containing the HBV-core coding regions was isolated from HBV-containing DNA. This fragment was ligated together with the 4.5 kb fragment containing the MT-promoter and the pBR residue (described in 1).

2 μl of the 1.8 kb fragment were mixed with 3 μl of the 4.5 kb fragment and ligated together in a total volume of 10 μl ligation buffer, containing 2 units T4-DNA ligase and 2 mM ATP at 14° C. overnight.

The ligation mixture was added to 150 μl competent bacterial cell suspension for DNA up-take. After the DNA up-take the bacterial cells were spread on LB agar plates containing 50 μl/ml ampicillin at volumes of 50 to 300 μl cell suspension per plate. The agar plates were incubated at 37° C. overnight. Single isolated bacterial colonies were screened for the presence of a plasmid containing the desired fragments.

3. Screening for Desired Plasmid Containing Bacterial Colonies

Single colonies were picked with a toothpick and transferred to a LB-ampicillin medium containing tube (5 ml). The tubes were incubated overnight at 37° in a rapidly shaking environment. A mini-plasmid preparation of each grown bacterial suspension was made. The different resulting DNAs were proved by digestion with the restriction endonuclease BglII. Two molecules were expected, a 400 bp fragment and a 5.9 kb fragment. The digestion was analysed by agarose gel electrophoresis. Plasmid DNA was isolated from the bacterial cells.

4. Insertion of a Neomycin Selection Marker

The plasmid resulting from (3) above was linearized by digestion with the restriction enzyme EcoRI. The reaction was performed in a total volume of 50 μl and a final concentration of 1 μg/μl plasmid DNA. 50 units of EcoRI were added and the digestion was proved after incubation at 37° C. for three hours by agarose gel electrophoresis. The reaction was stopped by adding 1 μl of 0.5 M EDTA and the DNA was precipitated with a final concentration of 0.3 M sodium acetate and 3–4 volumes of ethanol at −80° C. for 30 minutes. The precipitated DNA was dissolved in 50 μl distilled water.

2 μl of the linearized plasmid was mixed with 3 μl of the DNA fragment containing the methallothionein promoter and the neomycin selection gene (isolated from the plasmid pMT-neo-E (available from ATCC/Exogene) by digestion with the endonuclease EcoRI as a 3.9 kb fragment), and ligated together. Single bacterial colonies were screened for the presence of the desired plasmid.

5. Isolation of a Fragment Containing the U2 Promoter Sequence

The plasmid pUC-8-42 (available from Exogene) was digested with the restriction endonucleases EcoRI and ApaI. Two DNA molecules were generated. The fragment of interest contains the U2-promoter comprising 340 bp and is easily detectable from the other fragment (3160 bp). The digestion was performed in a total volume of 200 μl reaction buffer at a final concentration of 0.5 μg/μl DNA including 100 units of each restriction enzyme. The completion of the digest was checked after incubation at 37° C. for three hours by agarose gel electrophoresis in a 0.7% agarose gel. The reaction was stopped by adding 4 μl 0.5 M EDTA. The 340 bp fragment was separated from the plasmid DNA by preparative 1.2% agarose gel electrophoresis. The DNA was eluted from the agarose gel on DE-81 Whatman filter paper from which the DNA was removed in a high salt buffer. The DNA was purified by a phenol/chloroform extraction and two ethanol precipitations.

6. Insertion of the Fragment Containing the Promoter Sequence into a Polylinker Plasmid The plasmid pSP165 (commercially available from Promega Biotec) containing a polylinker sequence (containing the following restriction sites: EcoRI, SacI, SmaI, AvaI, BamHI, BglII, SalI, PstI, HindIII) was linearized with the restriction enzyme EcoRI. The reaction was performed in a total volume of 50 μl and a final concentration of 1 μg/μl plasmid DNA. 50 units of EcoRI was added and the digestion was proved after incubation at 37° C. for three hours by agarose gel electrophoresis. The reaction was stopped by adding 1 μl of 0.5 M EDTA and the DNA was precipitated with a final concentration of 0.3 M sodium acetate and 3–4 volumes of ethanol at 80° C. for 30 minutes. The precipitated DNA was dissolved in 50 μl distilled water.

2 μl of plasmid DNA was mixed with 10 μl of the fragment DNA containing the U2 promoter sequence, and ligated together in a total volume of 25 μl of ligation buffer containing 2 units T4-DNA ligase and 2 mM ATP at 14° C. overnight. Thereafter, the DNA purified by phenol/chloroform extractions followed by two ethanol precipitations and dissolved in 10 μl distilled water. The resulting sticky ends of EcoRI and ApaI had to be converted into blunt ends and ligated. The sticky ends were converted into blunt ends by reaction with the Mung bean nuclease as follows: to 25 μl DNA (1 μg/μl concentration) in reaction buffer 20 units of enzyme were added to give a final concentration of 1% glycerol and a final reaction volume of 35 μl. After an incubation for 30 minutes at 30° C. the DNA was purified by phenol-chloroform extractions followed by two ethanol precipitations. The DNA was dissolved again in 5 μl of distilled water. The resulting blunt ends were ligated together in 15 μl reaction volume containing 10× more T4 ligase than used above and 2 mM ATP at 14° C. overnight.

The ligation mixture was added to 150 μl competent bacterial cell suspension for DNA up-take. After the DNA up-take the bacterial cells were spread on LB agar plates containing 50 μg/ml ampicillin at volumes of 50 to 300 μl cell suspension per plate. The agar plates were incubated at 37° C. overnight. Single isolated bacterial colonies were screened for the presence of a plasmid containing the desired U2 -promoter fragment. The resulting plasmid was isolated from the bacterial cells and characterized by restriction enzyme analysis.

7. Ligation of Synthetic Oligo-DNA-nucleotide 89 (SEQ ID No.:30) Together With MT-promoter Fragment (4.5 kb)

The 4.5 kb fragment (described in 1) containing the MT-promoter and a pBR residue were ligated together with the synthetic oligonucleotide 89 (SEQ ID No.:30). The ligation mixture was added to 150 µl competent bacterial cell suspension for DNA up-take. Single isolated bacterial colonies were screened for the presence of the desired plasmid. The new plasmid was proved by a digestion with the restriction endonucleases EcoRI and XbaI. Two molecules were expected, one 2.0 kb and one 2.6 kb.

8. Ligation of the Synthetic Oligonucleotide 101 (SEQ ID No.:32) Together With Plasmid (Described in 7)

The plasmid (described in 7) was digested with BglII and BamHI and a fragment of 13 nucleotides was removed (described in 1). The resulting fragment containing the first oligonucleotide 89 (SEQ ID No.:30), was ligated together with oligonucleotide 101 (SEQ ID No.:32), a BglII-BamHI fragment. After DNA up-take single cells were screened for the presence of the desired plasmid. The new plasmid was proved by a digestion with the endonucleases EcoRI and XbaI, or EcoRI and BglII.

9. Ligation of Synthetic DNA-oligonucleotide 99 (SEQ ID No.:31) to the 4.5 kb Fragment (Described in 1)

The 4.5 kb fragment (BglII-BamHI) was ligated together with the DNA oligonucleotide 99 (SEQ ID No.: 31). After screening of single bacterial colonies, containing different DNAs, the desired plasmid was characterized by digestion with EcoRI, resulting in two fragments, 1.9 kb and 2.7 kb, and by positive linearization with BglII or BamHI.

The new plasmid was then digested with PstI and BamHI. Two molecules were expected, one 2.6 kb fragment, containing a pBR residue, the MT-promoter and the oligonucleotide and a 2.0 kb pBR residue. The 2.6 kb fragment was isolated.

10. Ligation of the 2.6 kb Fragment of the Plasmid Described in 9, with a Fragment Isolated from Plasmid (Described in 8)

The plasmid (described in 8) containing the DNA oligonucleotides 89 and 101 (SEQ ID No.:30 and 32, respectively) was digested with PstI and BglII. Two fragments were expected. A 2.5 kb fragment containing a pBR residue and the MT-promoter and 2.2 kb fragment, containing a pBR residue and both oligos.

This 2.2 kb fragment was ligated together with the 2.6 kb fragment, containing the pBR residue, the MT-promoter and oligo 99 (SEQ ID No.:31) described in 8.

After screening for the desired plasmid, it was characterized by restriction endonuclease digestion with BglII-XbaI. Two fragments were expected, a 270 bp fragment of the oligo-DNA-nucleotides and a 4.5 kb fragment of the MT-promoter and the pBR.

11. Ligation of the 2.3 kb HBV BglII-BglII Fragment

A 2.3 kb BglII-BglII fragment containing the HBV pre-S1, pre-S2 and S coding regions was isolated from HBV-containing DNA. The 2.3 kb fragment was ligated together with the 4.5 kb fragment (obtained as described in 1) containing the methallothionein promoter.

2 µl of the 2.3 kb fragment was mixed with 3 µl of the 4.5 kb fragment and ligated together in a total volume of 10 µl ligation buffer, containing 2 units T4-DNA ligase and 2 mM ATP at 14° C. overnight.

The ligation mixture was added to 150 µl competent bacterial cell suspension for DNA up-take. After the DNA up-take the bacterial cells were spread on LB agar plate containing 50 µg/ml ampicillin at volumes of 50 to 300 µl cell suspension per plate. The agar plates were incubated at 37° C. overnight. Single isolated bacterial colonies were screened for the presence of a plasmid containing the desired fragment.

12. Conversion of a Part of the HBV-gene Sequence with HBV-core Epitopes

The plasmid resulting from 11 above was digested with the endonucleases BglII and XbaI. Two molecules were expected, one 550 bp fragment and a 6.25 kb fragment which was isolated after agarose gel electrophoresis.

The 6.25 kb fragment was ligated together with the 270 bp fragment (after digestion with BglII and XbaI and fragment isolation as described above) of the plasmid described in 10, coding for an epitope part of the HBV-core gene.

The ligation mixture was added to 150 µl competent bacterial cell suspension for DNA up-take. Single isolated bacterial colonies were screened for the presence of the desired plasmid. The new plasmid was proved by a digestion with BamHI. Three molecules were expected, a 950 bp, a 450 bp and a 5,150 bp fragment.

13. Preparation of a "Vehicle" Plasmid

The plasmid (described in 11) was digested with EcoRI and XbaI. Two molecules were expected, one 2,450 bp fragment and a 4,350 bp fragment which was isolated after gel electrophoresis.

This 4,350 bp fragment was ligated together with the oligo-DNA-nucleotide 39 (SEQ ID No:29) coding for the entire DNA-sequence of HBV-S-gene from ATG to the XbaI site, wherein the ATG was changed into ATA.

14. Core-epitope Upstream of the Entire HBV-S Gene

This "vehicle" plasmid was then digested with PstI and XbaI, two molecules were expected, one 600 bp plasmid residue and a 3,850 bp fragment which was isolated and ligated together with a PstI-XbaI fragment of 2,800 bp (2,700 bp) isolated after digestion of the plasmid described in 10.

After screening for the desired plasmid, it was characterized by restriction endonuclease digestion with EcoRI and XbaI, EcoRI and BglII and BamHI.

15. Insertion of a Selection Marker

The plasmid (described in 14) was linearized with Eco RI. The reaction was performed in a total volume of 50 µl and a final concentration of 1 µg/µl plasmid DNA. 50 units of EcoRI were added and the digestion was proved after incubation at 37° C. for three hours by agarose gel electrophoresis.

The reaction was stopped by adding 1 µl of 0.5 M EDTA and DNA was precipitated with a final concentration of 0.3 M sodium acetate and 3–4 volumes of ethanol at −80° C. for 30 minutes. The precipitated DNA was dissolved in 50 µl distilled water.

2 µl of the linearized plasmid was mixed with 3 µl of the DNA fragment containing the methallothionein promoter and the neomycin selection gene (described in 4) and ligated together. Single bacterial colonies were screened for the desired plasmid which was isolated, purified and characterized.

Each gene construct described above can be constructed also with the U2-promoter whereby the MT-promoter-containing DNA fragment, after digestion with EcoRI and BglII, is replaced by a DNA fragment containing the U2-promoter isolated after digestion with EcoRI and BglII.

16. Isolation of the *E coli* Xanthine Quanine Phosphoribosyl Transferase (Egpt) Selection Gene The fragment containing the egpt selection gene was isolated after digestion of the plasmid pMSG with BamHI and BglII (1.8 kb) and ligated together with a 4.5 kb fragment (BglII-BamHI, described in 1) containing the MT-promoter.

After screening for the desired plasmid it was isolated, purified and finalized by a conversion of the BamHI site into an EcoRI site.

17. Isolation of Desired DNA Sequences by PCR-method

One DNA fragment (400 bp) was isolated after gel electrophoresis. It was generated by PCR-method (described in Example 5) by using the specific oligonucleotides 131 and 132 (SEQ ID No.:33 and 34) as primers.

The DNA fragemnt was digested with the endonucleases BamHI and XbaI and then purified by gel electrophoresis. The isolated PCR-fragment was ligated together with a 6.25 kb fragment which was isolated from the plasmid (described in 13) after digestion with BglII and XbaI. After DNA up-take and bacterial transformation the single bacterial colonies were screened for the desired plasmid.

18. Insertion of a Selection Marker

The plasmid (described in 17) was finalized by adding a selection gene to the plasmid (described in 15).

19. Isolation of the H2K Promoter

The H2K promoter was isolated as an EcoRI and BglII fragment (2 kb) from pSP65H2 (available from Exogene).

In all constructs described all promoters are replaceable as EcoRI/BglII fragments.

20. Conversion of a Part of the HBV-gene Sequence

The plasmid resulting from 11) above was digested with the endonucleases BglII and XbaI. Two molecules were expected, one of which is a 6.250 kb fragment which was isolated after agarose gel electrophoresis.

The 6.250 kb fragment was ligated together with oligo-DNA-nucleotide 23 (SEQ ID No.:28). The ligation mixture was added to 150 μl competent bacterial cell suspension for DNA up-take. Single isolated bacterial colonies were screened for the presence of the desired plasmid. The new plasmid was proven by a digestion with the endonucleases EcoRI and BglII. Two molecules were expected, one 1,9 kb and one 4.450 kb.

21. Insertion of a Egpt Selection Marker

The plasmid (described in 20) was linearized with EcoRI. The reaction was performed in a total volume of 100 μl and a final concentration of 0.6 μg/μl plasmid DNA. 60 units of EcoRI were added and the digestion was proved after incubation at 37° C. for three hours by agarose gel electrophoresis. The reaction was stopped by adding 2 μl of 0.5 M EDTA and the DNA was precipitated with a final concentration of 0.3 M sodium acetate and 4 volumes of ethanol at −80° C. for 1 hour. The precipitated DNA was dissolved in 50 μl distilled water.

2 μl of the linearized plasmid was mixed with 3 μl of the DNA-fragment (3.7 kb) containing the methallothionein promoter and the egpt selection gene (described in 16) by digestion with EcoRI and ligated together. Single colonies were screened for the presence of the desired plasmid. Each of the described gene constructs in Table III are preparable in the same way as described above.

EXAMPLE 4

Transfection of Mammalian Cells with Constructs of the Present Invention

In order to achieve secretion of substantial amounts of the HBV peptides encoded by constructs of the present invention, mammalian cells must be transfected with a DNA construct of the present invention. The cotransfection was performed in two steps (i.e. a separate transfection for each construct) or in a single step (i.e. one transfection using preparation of both constructs). Cotransfection was confirmed either by use of different selection markers on the two constructs or by detection of secretion of expression products of both constructs by immunoassay.

Alternatively, a sequence encoding the HBV peptide sequence of the present invention and a separate sequence encoding the entire S or core or HAV protein could be combined in a single construct.

EXAMPLE 5

Polymerase Chain Reaction (PCR)

The polymerase chain reaction allows to amplify specific DNA necleotide sequences of a selected region of a known genomic sequence in vitro by more than a millionfold (Thomas J. White, Norman Arnleim, Henry A. Erlich 1989: The polymerase chain reaction. Technical Focus, Vol. 5. No. 6; S. Kwok and R. Higuchi 1989: Avoiding false positives with PCR. Nature, Vol. 339, pp 237–238).

DNA isolated from cells or plasmid DNA is treated to separate its complementary strands. These strands are then annealed with an excess of two DNA oligonucleotides (each 20–25 base pairs long) that have been chemically synthesized to match sequences separated by X nucleotides (where X is generally between 50 to 2,000 base pairs).

The two oligonucleotides serve as specific primers for in vitro DNA synthesis catalysed by DNA polymerase which copies the DNA between the sequences corresponding to the two oligonucleotides. If the two primer oligonucleotides contain the correct sequence it is possible to create new digestion sites at the 5' and 3'.

After multiple cycles of reaction, a large amount of a DNA fragment of the desired length was obtained, purified by gel electrophoresis and characterized by restriction enzyme digestion and agarose gel electrophoresis. The amplified, purified DNA fragment was then used to ligate it together with other fragments i.e. plasmid.

The PCR-DNA fragments were amplified with blunt end. To get sticky end (for the ligation procedure) the fragment has to be digested with the desired endonucleases and purified again.

The PCR-reaction will work for 20 to 30 cycles. One cycle is separated into three steps with different reaction times and different reaction temperatures which is controlled by a PCR-thermo-cycler. The first step is "Denaturation" of the matrix-DNA (1 min-95° C.), the second step is "Hybridisation" of matrix DNA and primers (1 min/55° C.) followed by "Polymerisation" (2 min/72° C.).

The final volume for one assay is 30 μl for example, which contains the following final concentrations: PCR-buffer (1×), nucleotide-mix with 200 μM of each of the four nucleotides, 200 ng for 30 μl of each of the two primers, 0.5 units Taq-Polymerase per 30 μl aqua bidest.

EXAMPLE 6

Culturing of Transfected Cells to Secrete Protein

The recipient cells (C127 or CHO-cells available from ATCC) were seeded in normal growth medium (DMEM+ 10% Fetal Calf Serum, Glucose and Glutamine) into pet-ridishes (1–2×10⁶ cells per dish, φ10 cm) at day 1. The next day the medium was removed (4 hours before the DNA precipitate was added onto the cells), and the cells were washed twice with 1×PBS. Then 8 ml DMEM without FCS were added, 4 hours later the DNA precipitate (prepared as described below) was added to the cells. Again after 4 hours the medium was removed, 3 ml of Glycerol-Mix (50 ml 2×TBS buffer, 30 ml glycerol, 120 ml distilled water) were added. The Glycerol-Mix was immediately removed after an incubation at 37° C. for 3 minutes and the cells were washed with 1×PBS. The cells were cultivated overnight with 8 ml of DMEM with 10% FCS.

After 48 hours, the cells were recovered from the dish by treating with Trypsin-EDTA-Solution (0.025% Trypsin +1 mM EDTA). Afterwards, to remove the Trypsin-EDTA the cells were washed with 1×PBS, suspended in DMEM with 10% FCS and distributed into 24 costar-well-plates (cells from one dish into four 24-well-plates).

When the cells had grown well, selection medium was added (concentration 0.5–1 mg/ml of neomycin or: xanthine (250 μg/ml), hypoxanthine (15 μg/ml) or adenine (25 μg/ml), thymidine (10 μg/ml), aminopterine (2 μg/ml), mycophenolic acid (25 μg/ml) for eco-gpt, for example). The medium was changed every week. The first growing cell colonies were seen after 2 weeks.

To 10 μg of plasmid DNA and 20 μg of carrier-DNA (salmon sperm DNA, calf-thymus DNA) TE-buffer (10 mM Tris-HCl, 1 mM EDTA, pH 7.05) was added to a final volume of 440 μl and mixed together with 60 μl 2 M $CaCl_2$. Then the same amount of 2×TBS (Hepes 50 mM, NaCl 280 mM, $Na_2HPO_4$ 1.5 mM, pH 7.05) was added and mixed well. The precipitation solution was incubated for 30 minutes at 37° C. and added directly to the cells which were to be transfected.

EXAMPLE 7

Preparation of the Adjuvant of Purified Particles

To the desired concentration of antigen suspended in sterile saline, 1:10,000 volume Thimerosol, 1/10 volume of filter-sterilized 0.2 M $KAl(SO_4)_2·12 H_2O$ were added. The pH was adjusted to 5.0 with sterile 1 N NaOH and the suspension was stirred at room temperature for 3 hours. The alum-precipitated antigen was recovered by centrifugation for 10 minutes at 2,000 rpm, resuspended in sterile normal saline containing 1:10,000 Thimerosol and aliquoted under sterile conditions.

EXAMPLE 8

Purification of Hepatitis-B-core Antigen

The cell supernatant of HB-core-antigen-secreting cells was collected and concentrated by ultrafiltration. The concentrate was cleared by centrifugation at 20,000 rpm for 15 minutes at 4° C. in a Beckman SW28 rotor.

Particle formation was tested by sucrose density centrifugation (0–45% sucrose) in a Beckman SW28 rotor for 24 hours at 28,000 rpm and 4° C. The gradient was fractionated and the single fractions were analyzed by Elisa.

EXAMPLE 9

The following tables give some results of Elisa analysis of immunogenic particles of the present invention as described below:

Table IV shows the Elisa data of the purified HBs-antigen particle produced from any HBV-sequence construct of the present invention including the pre-S1 epitopes and the S region with the anti-pre-S1 monoclonal antibody MA 18/7 and the anti-HBs monoclonal antibody G022.

Table IV shows the fractions (21) collected after CsCl density gradient.

TABLE IV-1

| CsCl-gradient Fraction No. | Elisa Measurement (E = 492) Monoclonal Antibody 18/7 |
| --- | --- |
| 13 | 0.092 |
| 14 | 0.210 |
| 15 | 0.388 |
| 16 | 1.662 |
| 17 | 2.604 |
| 18 | 0.648 |
| 19 | 0.031 |

TABLE IV-2

| CsCl-gradient Fraction No. | Elisa Measurement (E = 492) Monoclonal Antibody G022 |
| --- | --- |
| 13 | 0.136 |
| 14 | 0.426 |
| 15 | 0.822 |
| 16 | 1.970 |
| 17 | 2.954 |
| 18 | 0.967 |
| 19 | 0.076 |

Table V shows the Elisa data of the purified HB-core-antigen particles produced from any HB-core-sequence constant of the present invention with polyclonal antibodies against HB-core and with monoclonal antibody G022 HB—S—Ag.

TABLE V-1

| Sucrose Gradient Fraction No. | Elisa Measurement (E = 492) Polyclonal Antibodies |
| --- | --- |
| 6 | 0.25 |
| 7 | 0.922 |
| 8 | 1.423 |
| 9 | 1.5 |
| 10 | 1.5 |
| 11 | 1.28 |
| 12 | 0.466 |

TABLE V-2

| Sucrose Gradient Fraction No. | Elisa Measurement (E = 492) Monoclonal Antibody G022 |
| --- | --- |
| 6 | 0.020 |
| 7 | 0.024 |
| 8 | 0.018 |
| 9 | 0.011 |
| 10 | 0.015 |
| 11 | 0.020 |
| 12 | 0.022 |

EXAMPLE 10

Studies of administering Hepa-Care in chimpanzees:

Hepa-Care are particles presenting hepatitis B surface antigens (S1 and S) in a specific formulation (ratio 50:50), which are used for the treatment of chronic carriers of hepatitis virus.

Experiment 1

A Hepatitis-B-carrier chimpanzee 1 was treated (intramuscularly) with Hepa-Care at time 0, 4, and 8 weeks with a dosage of 18 μg per injection.

Figure 4:
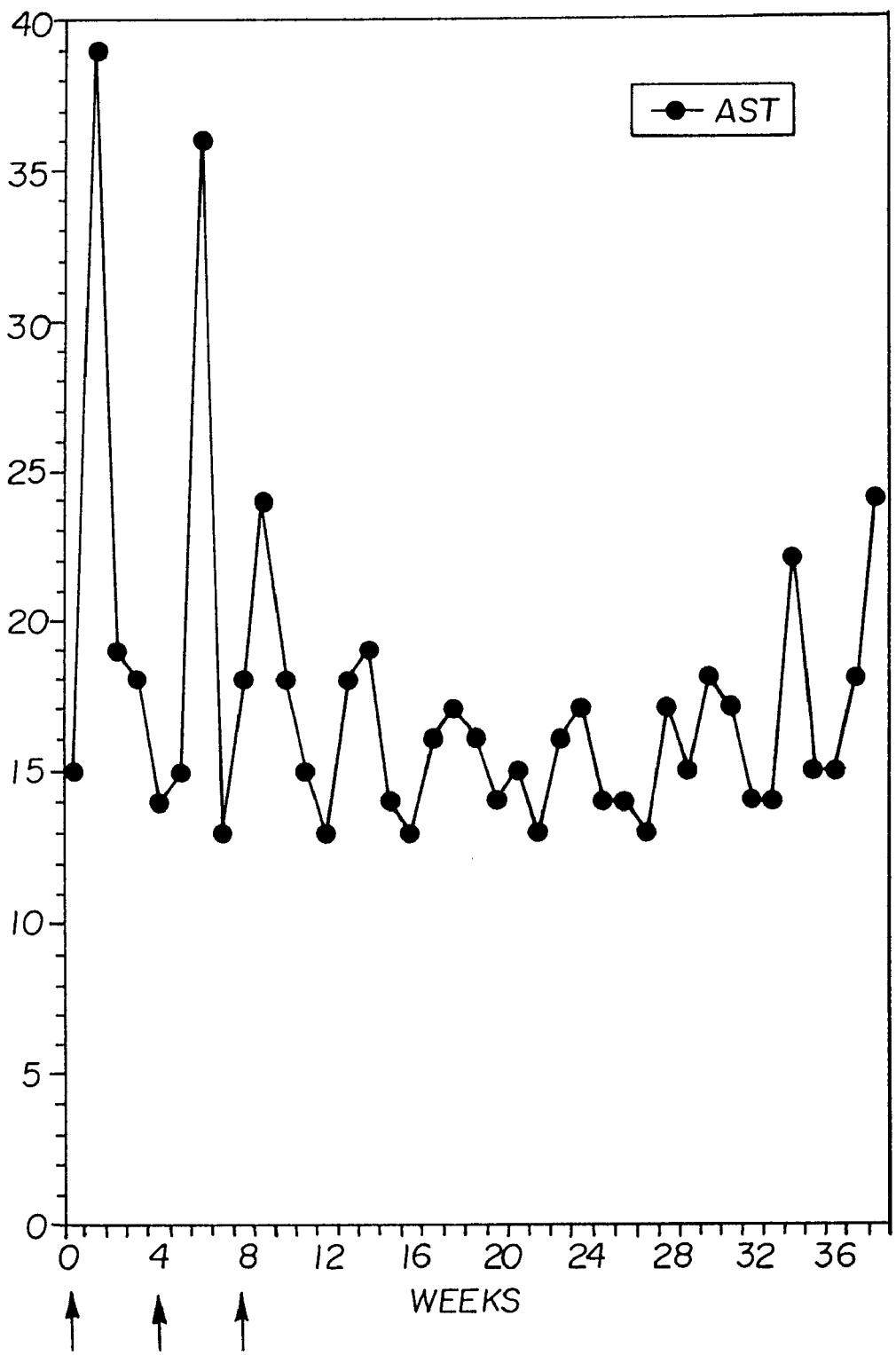
FIG. 4 shows the AST values of chimpanzee 1 during the Hepa-Care treatment (described in Example 10/1).
Figure 5:
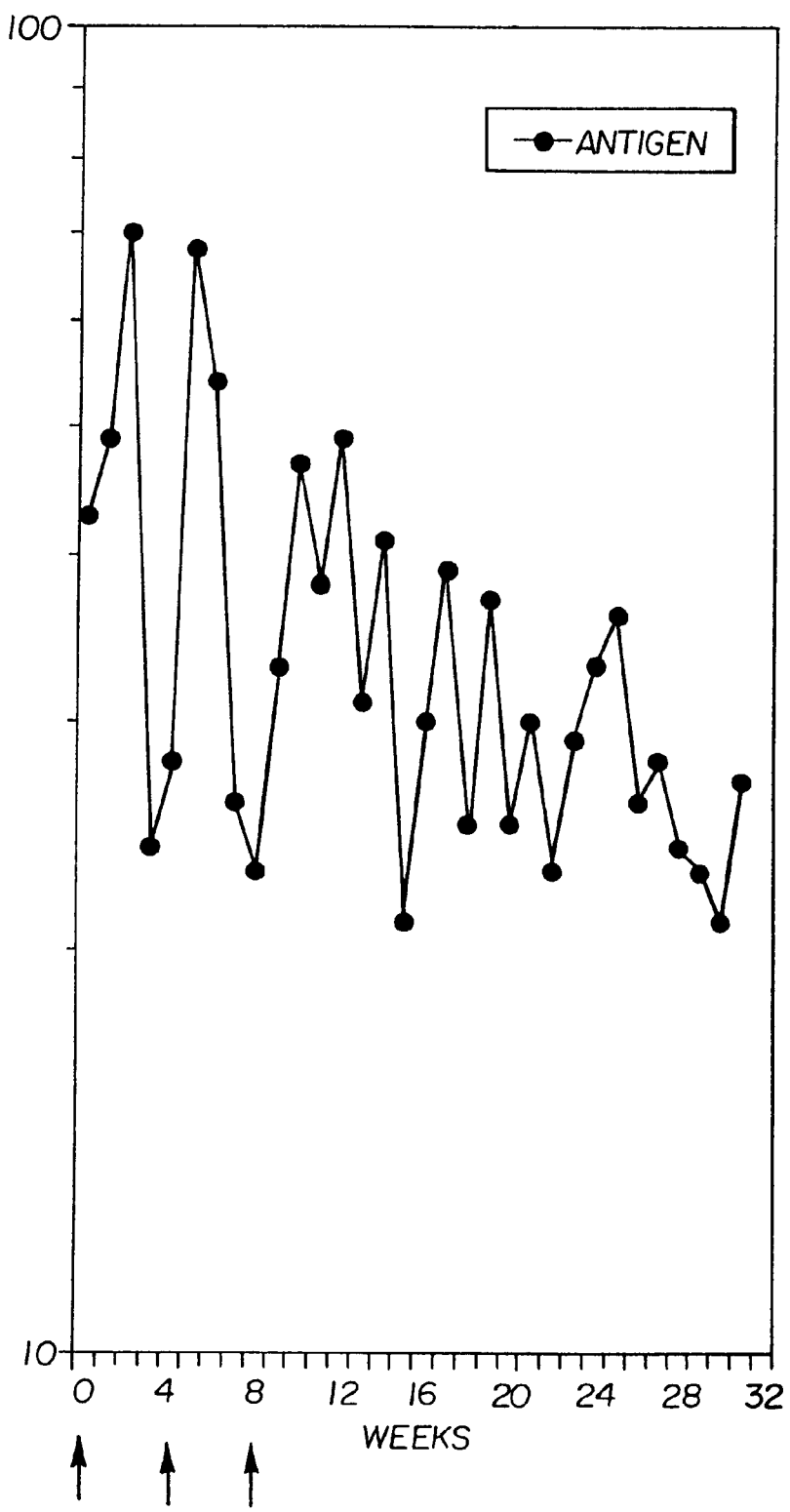
FIG. 5 shows the antigen values of chimpanzee 1 during the Hepa-Care treatment (described in Example 10/1)

The liver enzymes were monitored (FIG. 4) as well as the hepatitis-B antigen level (FIG. 5).

Experiment 2

Figure 6:
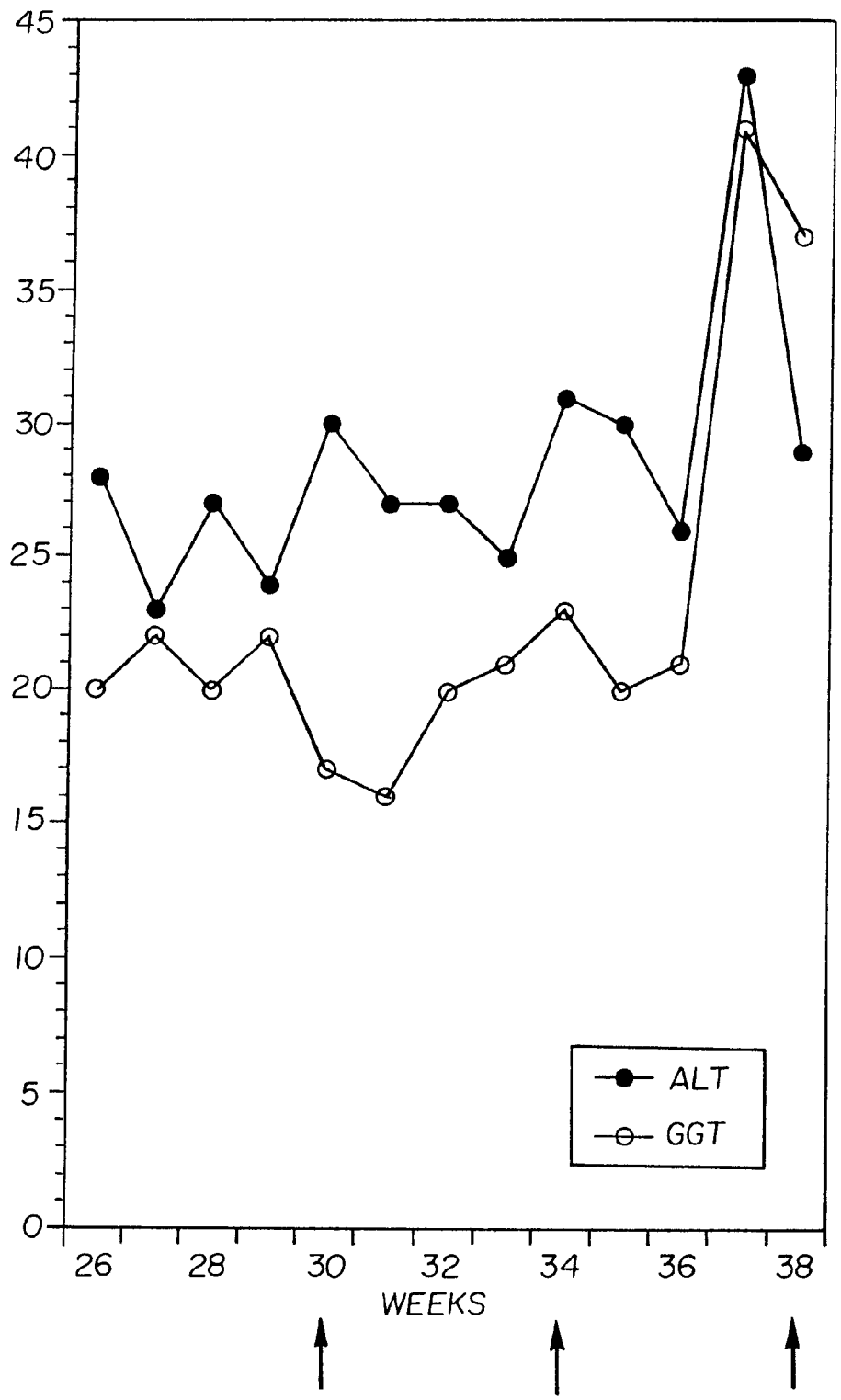
FIG. 6 shows values of liver enzymes ALT and GGT of chimpanzee 1 booster treated three times with Hepa-Care (described in Example 10/2).

Chimpanzee 1 after treatment described above was given a booster treatment at week 30, 34, and 38. The results are shown in FIG. 6.

Experiment 3

Figure 7A:
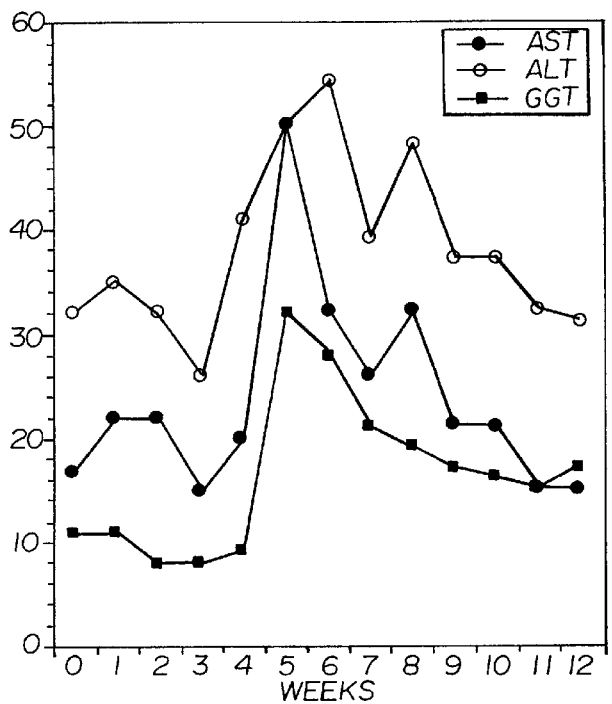
FIG. 7 shows values of liver enzymes ALT, AST, and GGT and of antigen of chimpanzee 2 during the Hepa-Care treatment (described in Example 10/3).
Figure 7B:
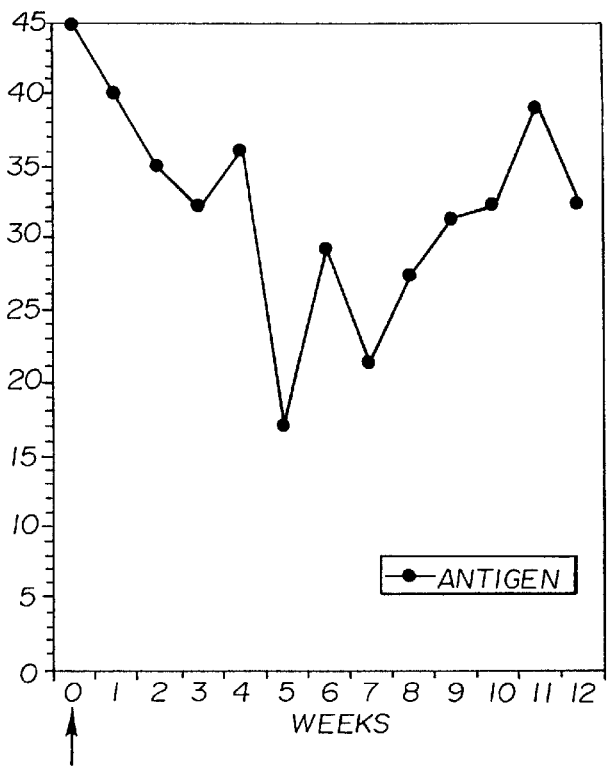

Chimpanzee 2 was treated with Hepa-Care, but contrary to chimpanzee 1 it was given intravenously. The dosage was 2 mg. The results are shown in FIG. 7.

Figure 8:
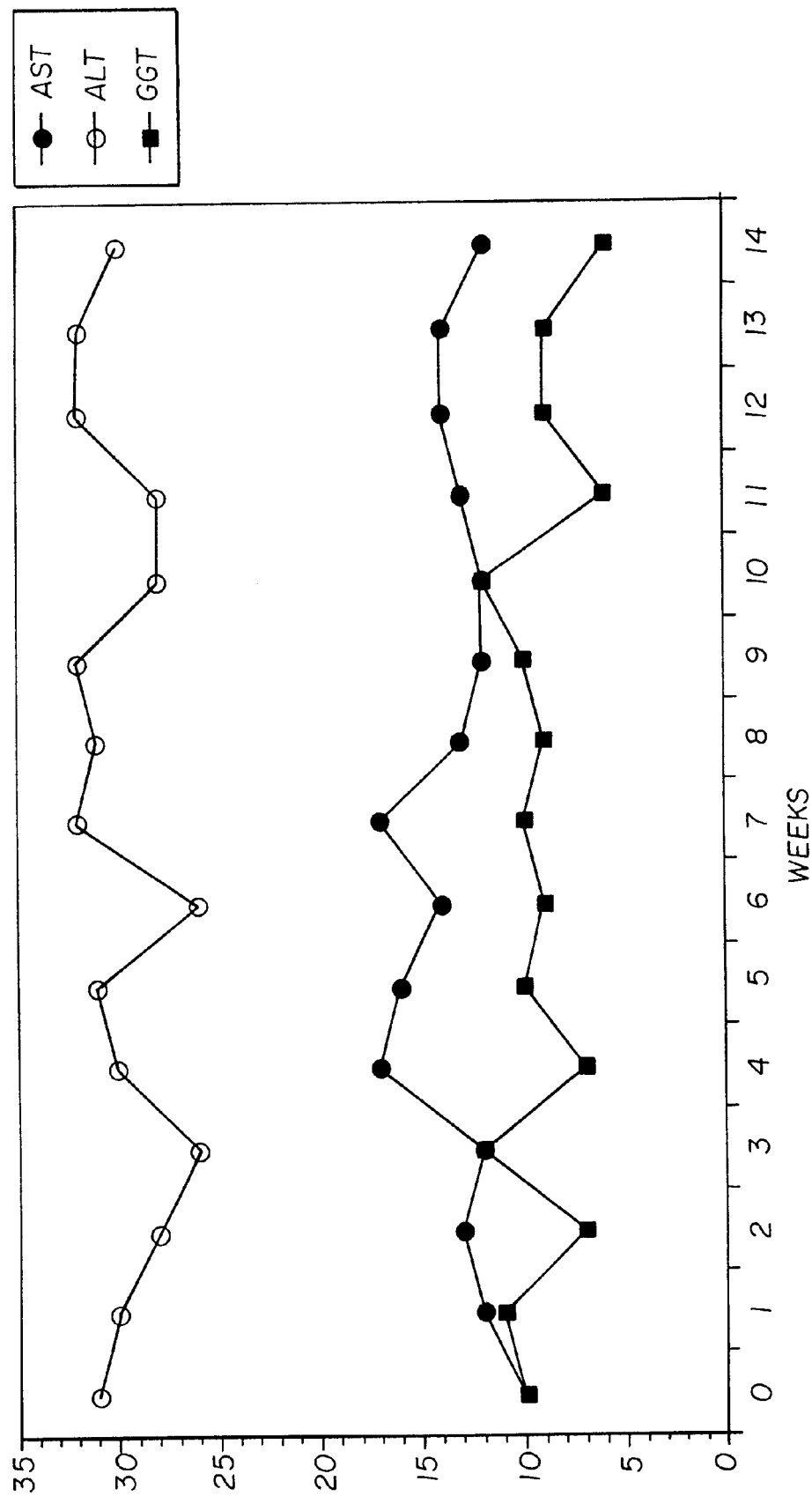
FIG. 8 shows the liver enzymes as determined for an untreated control chimpanzee (described in Example 10/3).

From a control chimpanzee 3 the liver enzymes were also monitored and shown in FIG. 8.

EXAMPLE 11

Treatment with Hepa-Care: (for definition see Example 10)

Figure 9:
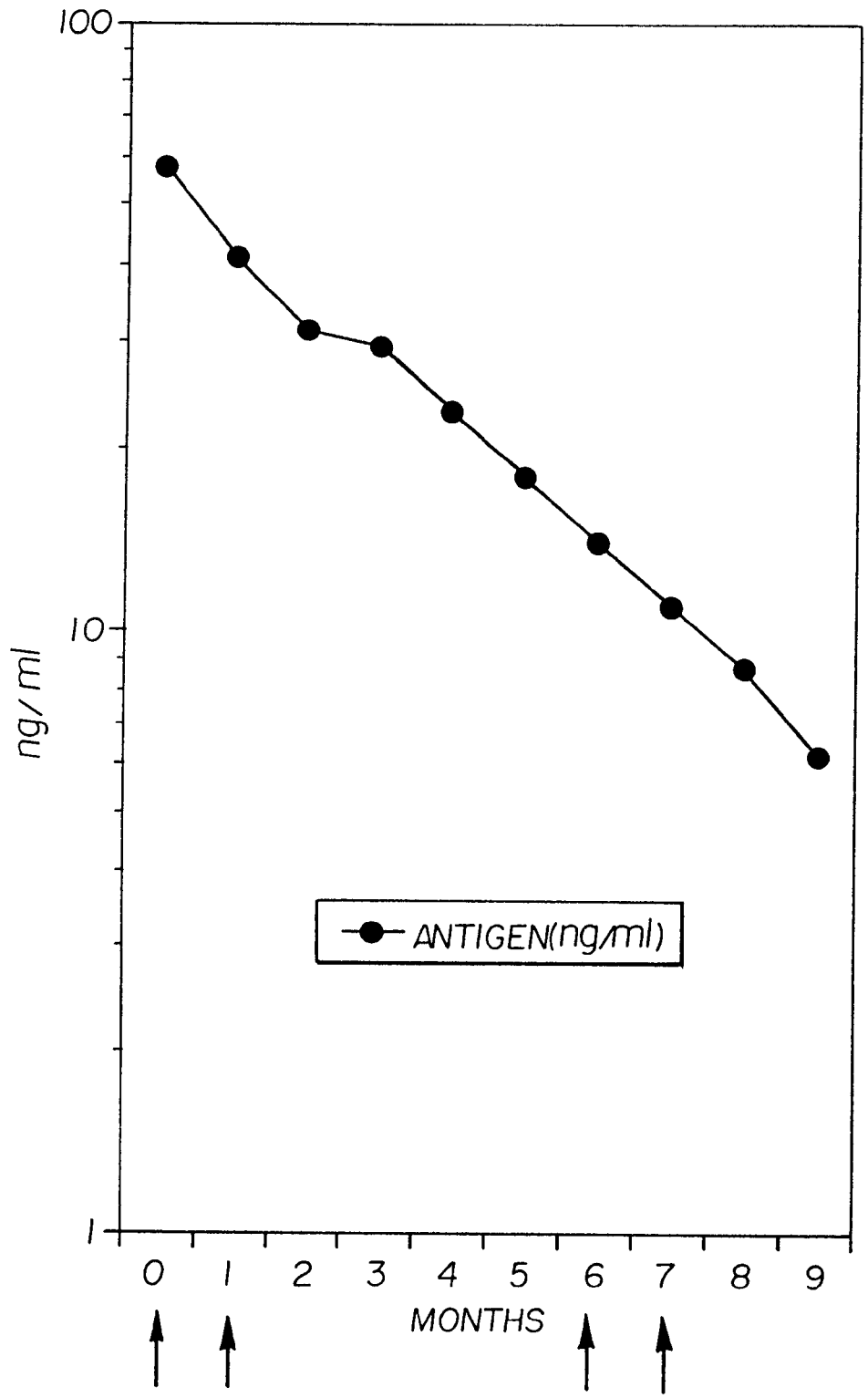
FIGS. 9 & 10 show the antigen and antibody titers of patient 1 during the Hepa-Care treatment, respectively (described in Example 11).
Figure 10:
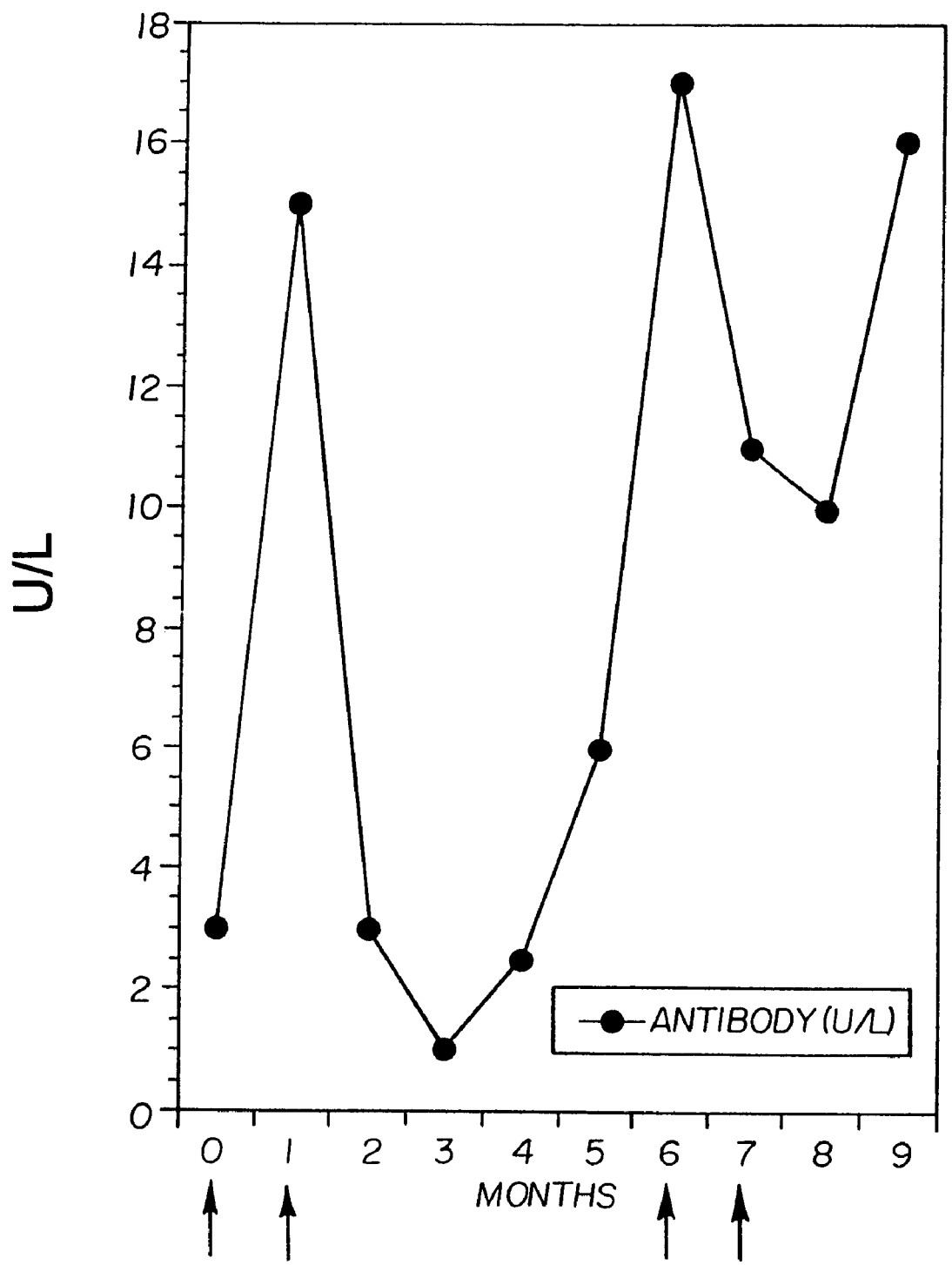

Patient 1 (male, age=65 years, disease for 2 years):

| Hepatitis-B parameters: | HBSAg | pos. |
|---|---|---|
| | anti-HBs | neg. |
| | HBeAg | neg. |
| | anti-HBe | pos. |
| | anti-HBc | neg. | was treated (i.m.) with Hepa-Care at month 0, 1, 6, and 7. The results of the antigen and antibody measurements are given in FIGS. 9 and 10.

Figure 11:
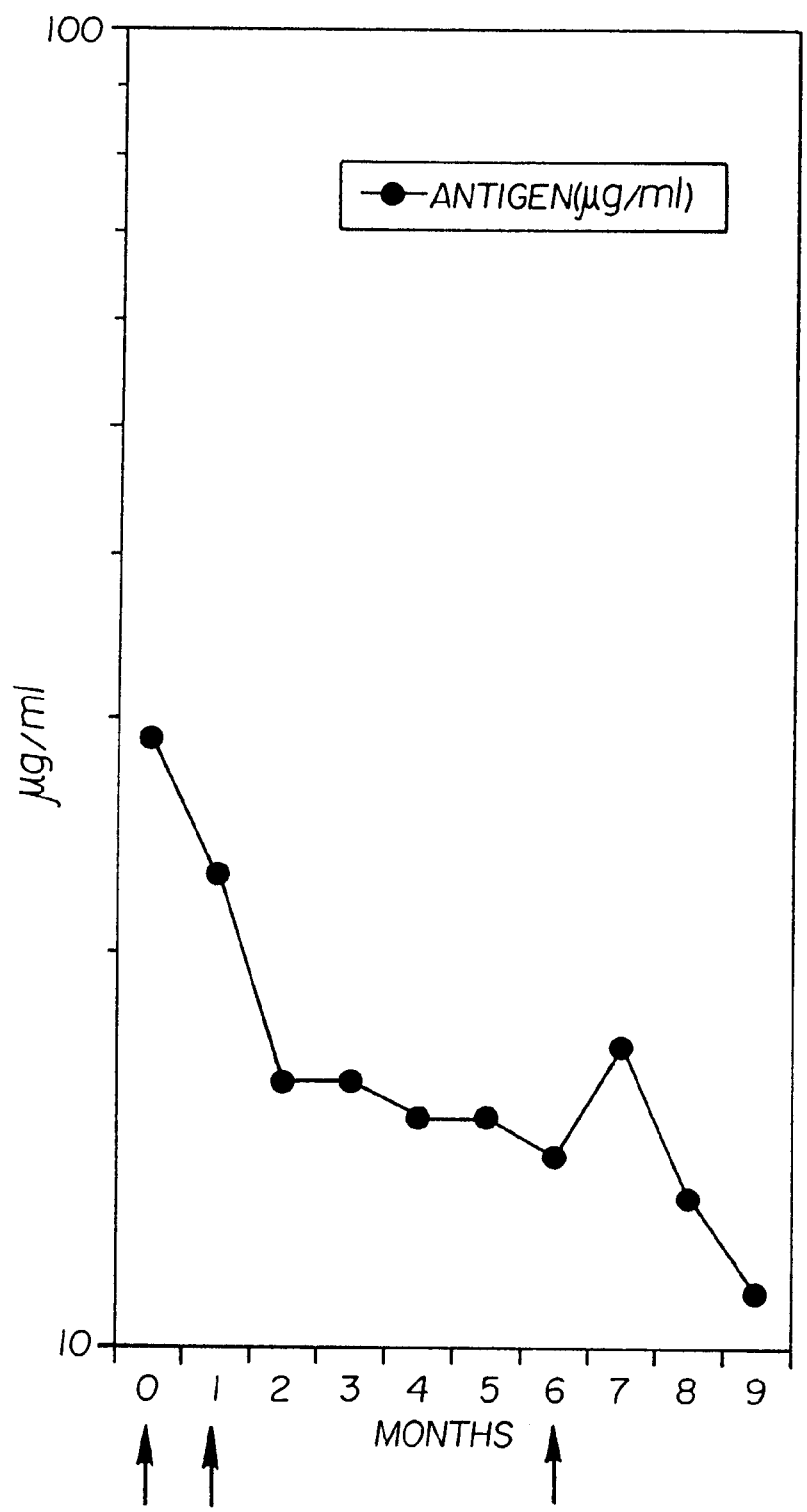
FIGS. 11 & 12 show the antigen and antibody titers of patient 2 during the Hepa-Care treatment, respectively (described in Example 11).
Figure 12:
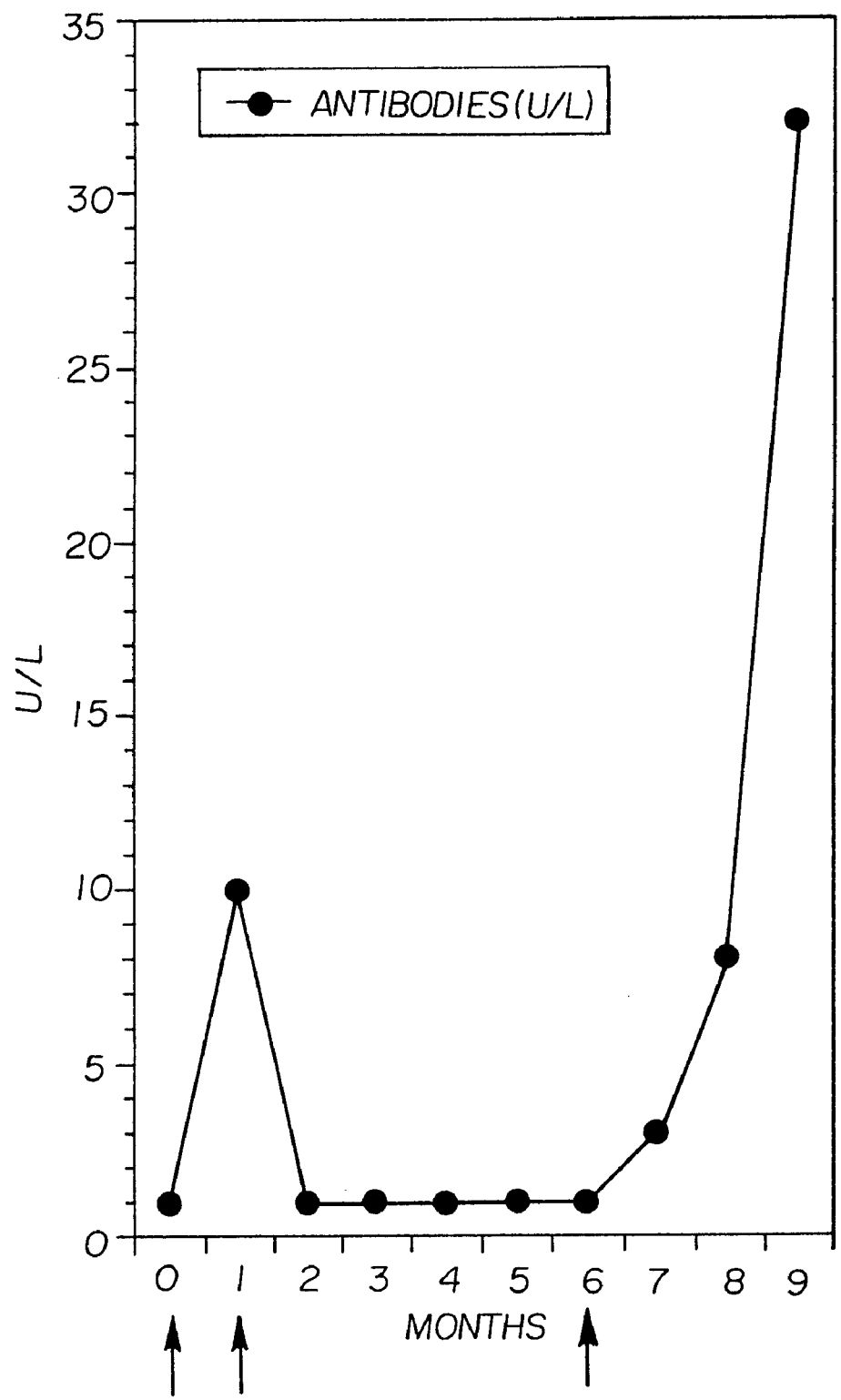

Patient 2 (female, age=48 years, disease for 12 years):

| Hepatitis-B parameters: | HBSAg | pos. |
|---|---|---|
| | HBeAg | neg. |
| | anti-HBS | neg. |
| | anti-HBe | pos. |
| | anti-HBc | pos. | was treated (i.m.) with Hepa-Care at month 0, 1, and 6. Results of antigen and antibody measurements are shown in FIGS. 11 and 12.

Figure 13:
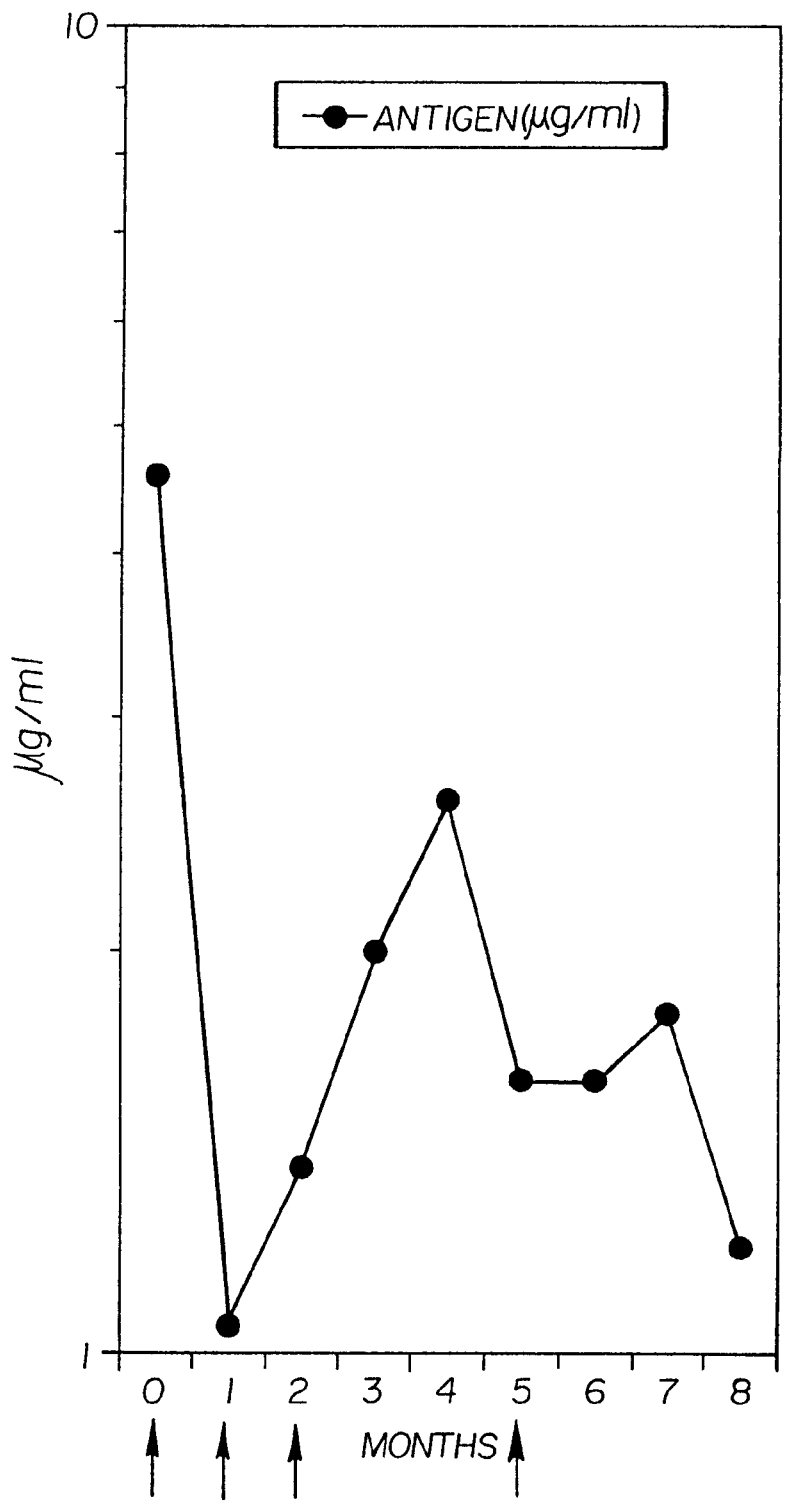
FIGS. 13 & 14 show the antigen and antibody titers of patient 2 during the Hepa-Care treatment, respectively (described in Example 11).
Figure 14:
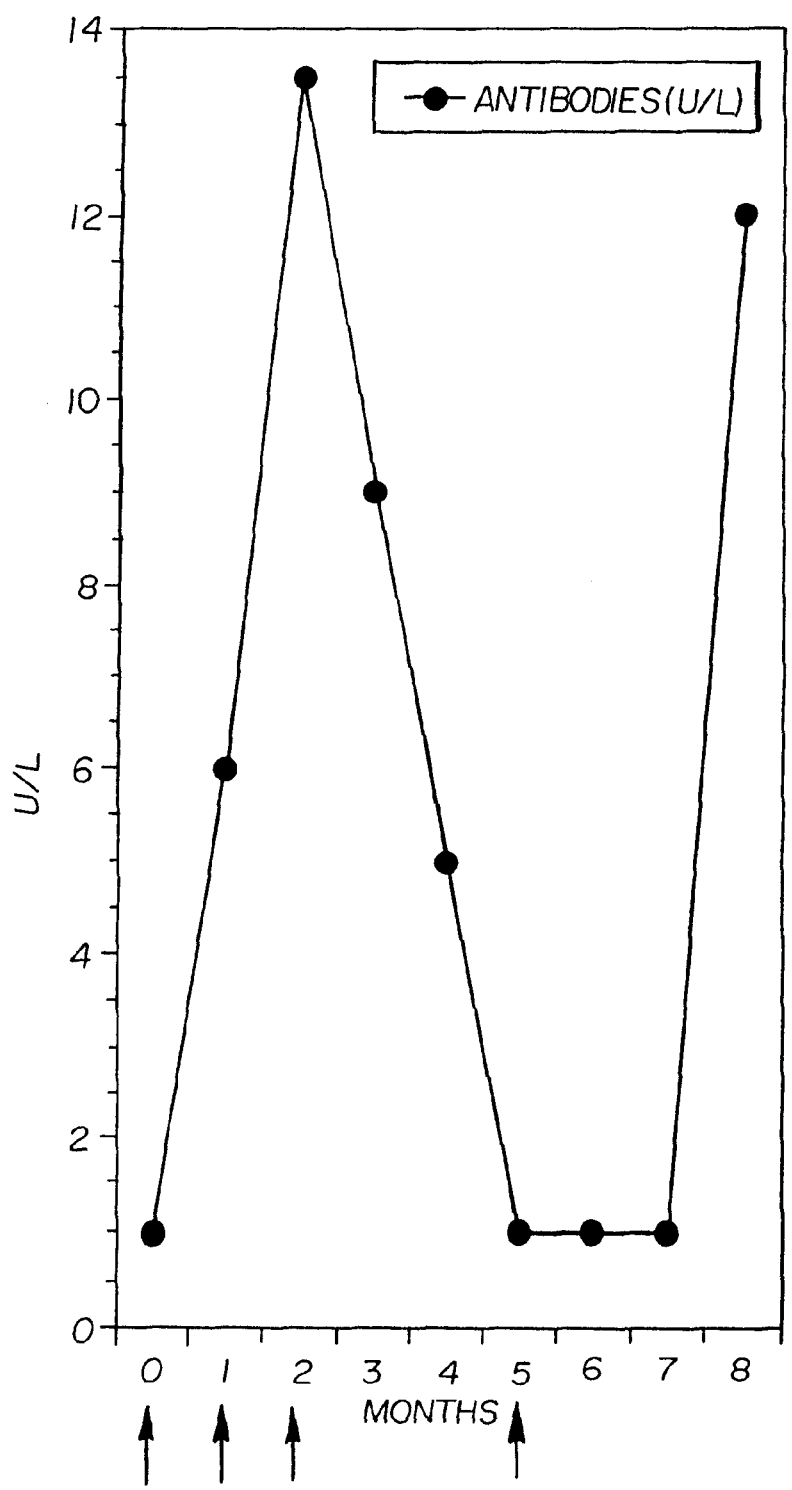

Patient 3 (female, age=41 years, disease for 5 years):

| Hepatitis-B parameters: | HBSAg | pos. |
|---|---|---|
| | HBeAg | neg. |
| | anti-HBs | neg. |
| | anti-HBe | pos. | was treated at month 0, 1, 2, and 5 with Hepa-Care (i.m.). The measured values of HBs antigen and anti-HBs antibodies are shown in FIGS. 13 and 14.

---

I claim:

1. A method of treating chronic hepatitis B comprising administering a composition to a patient having serum containing HBsAg, the composition comprising:
    (a) a polypeptide having one or more T-cell activating epitopes selected from HBV pre-S1 or HBV core T-cell activating epitopes; and
    (b) a carrier capable of presenting the polypeptide, wherein the polypeptide is bound to the carrier,
    wherein the method results in a decrease in the amount of HBsAg in the serum of the patient.

2. The method of claim 1, wherein the method results in the disappearance of the HBsAg from the serum of the patient.

3. The method of claim 1, wherein at least one of the one or more T-cell activating epitopes is an HBV pre-S1 epitope.

4. The method of claim 1, wherein at least one of the one or more T-cell activating epitopes is an HBV core epitope.

5. The method of claim 1, wherein the carrier is a particle of a hydrophobic polymer, an inorganic particle, a particle of a polysaccharide, or a polypeptide which forms particles.

6. The method of claim 1, wherein the carrier is a polypeptide which forms particles and which comprises a substantial part of or the complete amino acid sequence of an HBV S peptide.

7. The method of claim 6, wherein the polypeptide having one or more T-cell activating epitopes and the carrier polypeptide are connected by a peptide bond to form a fusion polypeptide.

8. The method of claim 1, wherein the carrier is a polypeptide which forms particles and which comprises a substantial part of or the complete amino acid sequence of an HBV core peptide.

9. The method of claim 8, wherein the polypeptide having one or more T-cell activating epitopes and the carrier polypeptide are connected by a peptide bond to form a fusion polypeptide.

10. The method of claim 7, wherein the fusion polypeptide has the following amino acid sequence:
    Met-Glu-Asn-Asn-Pro-Leu-Gly-Phe-Phe-Pro-Asp-His-Gln-Leu-Asp-Pro-Ala-Phe-Arg-Ala-Asn-Thr-Ala-Asn-Pro-Asp-Trp-Asp-Phe-Asn-Pro-Ser-Xaa;
    wherein Xaa is the amino acid sequence of amino acids 32 to 226 of an HBV S peptide.

11. A method of treating chronic hepatitis B comprising administering a composition to a patient having serum containing HBeAg, the composition comprising:
    (a) a polypeptide having one or more T-cell activating epitopes selected from HBV pre-S1 or HBV core T-cell activating epitopes; and
    (b) a carrier capable of presenting the polypeptide, wherein the polypeptide is bound to the carrier,
    wherein the method results in a decrease in the amount of HBeAg in the serum of the patient.

12. The method of claim 11, wherein the method results in the disappearance of the HBeAg from the serum of the patient.

13. The method of claim 11, wherein at least one of the one or more T-cell activating epitopes is an HBV pre-S1 epitope.

14. The method of claim 11, wherein at least one of the one or more T-cell activating epitopes is an HBV core epitope.

15. The method of claim 11, wherein the carrier is a particle of a hydrophobic polymer, an inorganic particle, a particle of a polysaccharide, or a polypeptide which forms particles.

16. The method of claim 11, wherein the carrier is a polypeptide which forms particles and which comprises a substantial part of or the complete amino acid sequence of an HBV S peptide.

17. The method of claim 16, wherein the polypeptide having one or more T-cell activating epitopes and the carrier polypeptide are connected by a peptide bond to form a fusion polypeptide.

18. The method of claim 11, wherein the carrier is a polypeptide which forms particles and which comprises a substantial part of or the complete amino acid sequence of an HBV core peptide.

19. The method of claim 18, wherein the polypeptide having one or more T-cell activating epitopes and the carrier polypeptide are connected by a peptide bond to form a fusion polypeptide.

20. The method of claim 17, wherein the fusion polypeptide has the following amino acid sequence:
    Met-Glu-Asn-Asn-Pro-Leu-Gly-Phe-Phe-Pro-Asp-His-Gln-Leu-Asp-Pro-Ala-Phe-Arg-Ala-Asn-Thr-Ala-Asn-Pro-Asp-Trp-Asp-Phe-Asn-Pro-Ser-Xaa;
    wherein Xaa is the amino acid sequence of amino acids 32 to 226 of an HBV S peptide.

21. A method of treating chronic hepatitis B comprising administering a composition to a patient having serum containing HBV DNA, the composition comprising:
    (a) a polypeptide having one or more T-cell activating epitopes selected from HBV pre-S1 or HBV core T-cell activating epitopes; and
    (b) a carrier capable of presenting the polypeptide, wherein the polypeptide is bound to the carrier,
    wherein the method results in a decrease in the amount of HBV DNA in the serum of the patient.

22. The method of claim 21, wherein the method results in the disappearance of HBV DNA from the serum of the patient.

23. The method of claim 21, wherein at least one of the one or more T-cell activating epitopes is an HBV pre-S1 epitope.

24. The method of claim 21, wherein at least one of the one or more T-cell activating epitopes is an HBV core epitope.

25. The method of claim 21, wherein the carrier is a particle of a hydrophobic polymer, an inorganic particle, a particle of a polysaccharide, or a polypeptide which forms particles.

26. The method of claim 21, wherein the carrier is a polypeptide which forms particles and which comprises a substantial part of or the complete amino acid sequence of an HBV S peptide.

27. The method of claim 26, wherein the polypeptide having one or more T-cell activating epitopes and the carrier polypeptide are connected by a peptide bond to form a fusion polypeptide.

28. The method of claim 21, wherein the carrier is a polypeptide which forms particles and which comprises a substantial part of or the complete amino acid sequence of an HBV core peptide.

29. The method of claim 28, wherein the polypeptide having one or more T-cell activating epitopes and the carrier polypeptide are connected by a peptide bond to form a fusion polypeptide.

30. The method of claim 27, wherein the fusion polypeptide has the following amino acid sequence:

Met-Glu-Asn-Asn-Pro-Leu-Gly-Phe-Phe-Pro-Asp-His-Gln-Leu-Asp-Pro-Ala-Phe-Arg-Ala-Asn-Thr-Ala-Asn-Pro-Asp-Asp-Phe-Asn-Pro-Ser-Xaa;

wherein Xaa is the amino acid sequence of amino acids 32 to 226 of an HBV S peptide.

31. A method of treating chronic hepatitis B comprising administering a composition to a patient having HBV DNA sequences integrated into the genome of the patient's liver cells, the composition comprising:

(a) a polypeptide having one or more T-cell activating epitopes selected from HBV pre-S1 or HBV core T-cell activating epitopes; and (b) a carrier capable of presenting the polypeptide, wherein the polypeptide is bound to the carrier, wherein the method results in a decrease in the amount of HBV DNA sequences integrated into the genome of the patient's liver cells.

32. The method of claim 31, wherein the method results in the disappearance of HBV DNA sequences integrated into the genome of the patient's liver cells.

33. The method of claim 31, wherein at least one of the one or more T-cell activating epitopes is an HBV pre-S1 epitope.

34. The method of claim 31, wherein at least one of the one or more T-cell activating epitopes is an HBV core epitope.

35. The method of claim 31, wherein the carrier is a particle of a hydrophobic polymer, an inorganic particle, a particle of a polysaccharide, or a polypeptide which forms particles.

36. The method of claim 31, wherein the carrier is a polypeptide which forms particles and which comprises a substantial part of or the complete amino acid sequence of an HBV S peptide.

37. The method of claim 38, wherein the polypeptide having one or more T-cell activating epitopes and the carrier polypeptide are connected by a peptide bond to form a fusion polypeptide.

38. The method of claim 31, wherein the carrier is a polypeptide which forms particles and which comprises a substantial part of or the complete amino acid sequence of an HBV core peptide.

39. The method of claim 38, wherein the polypeptide having one or more T-cell activating epitopes and the carrier polypeptide are connected by a peptide bond to form a fusion polypeptide.

40. The method of claim 37, wherein the fusion polypeptide has the following amino acid sequence:

Met-Glu-Asn-Asn-Pro-Leu-Gly-Phe-Phe-Pro-Asp-His-Gln-Leu-Asp-Pro-Ala-Phe-Arg-Ala-Asn-Thr-Ala-Asn-Pro-Asp-Trp-Asp-Phe-Asn-Pro-Ser-Xaa;

wherein Xaa is the amino acid sequence of amino acids 32 to 226 of an HBV S peptide.

* * * * *

UNITED STATES PATENT AND TRADEMARK OFFICE
CERTIFICATE OF CORRECTION

PATENT NO. : 6,020,167
DATED : February 1, 2000
INVENTOR(S) : Hans A. Thoma

It is certified that error appears in the above-identified patent and that said Letters Patent is hereby corrected as shown below:

Column 3, line 29, replace "sequences)" with --sequences(s)--.
Table III of Columns 9 and 10, line 37, replace "pre-cure" with --pre-core--.
Claim 30, line 5, (column 49, line 25) insert --Trp- -- after "Pro-Asp-".
Claim 37, line 1,(column 50, line 19) replace "38" with --36--.

Signed and Sealed this

Tenth Day of April, 2001

Attest:

NICHOLAS P. GODICI

*Attesting Officer*  *Acting Director of the United States Patent and Trademark Office*